(12) United States Patent
Sun et al.

(10) Patent No.: US 8,211,361 B2
(45) Date of Patent: Jul. 3, 2012

(54) N-HALAMINE-BASED RECHARGEABLE BIOFILM-CONTROLLING TUBULAR DEVICES, METHOD OF MAKING AND USING

(75) Inventors: Yuyu Sun, Sioux Falls, SD (US); Jie Luo, Sioux Falls, SD (US); Zhaobin Chen, Shanghai (CN)

(73) Assignee: Board of Regents, The University of Texas System, Austin, TX (US)

( * ) Notice: Subject to any disclaimer, the term of this patent is extended or adjusted under 35 U.S.C. 154(b) by 1047 days.

(21) Appl. No.: 12/056,124

(22) Filed: Mar. 26, 2008

(65) Prior Publication Data
US 2008/0268189 A1 Oct. 30, 2008

Related U.S. Application Data

(60) Provisional application No. 60/908,168, filed on Mar. 26, 2007.

(51) Int. Cl.
*A61L 2/16* (2006.01)

(52) U.S. Cl. ............................. 422/28; 422/29; 428/34.1

(58) Field of Classification Search .................... 422/28, 422/29; 428/34.1
See application file for complete search history.

(56) References Cited

U.S. PATENT DOCUMENTS

| | | | |
|---|---|---|---|
| 3,285,928 A | 11/1966 | Gubitz | |
| 3,488,701 A | 1/1970 | Herbes et al. | |
| 3,876,657 A | 4/1975 | Aelony et al. | |
| 3,971,757 A | 7/1976 | Rasberger | |
| 3,975,462 A | 8/1976 | Murayama et al. | |
| 4,091,223 A | 5/1978 | Zussman et al. | |
| 4,241,208 A | 12/1980 | Murayama et al. | |
| 4,785,055 A | 11/1988 | Dexter et al. | |
| 4,931,562 A | 6/1990 | Akabane et al. | |
| 5,057,562 A | 10/1991 | Reinert | |
| 5,459,145 A | 10/1995 | Saccomano et al. | |
| 5,490,983 A | 2/1996 | Worley et al. | |
| 5,580,872 A | 12/1996 | Chu et al. | |
| 5,670,064 A | 9/1997 | Nakata | |
| 5,670,646 A | 9/1997 | Worley et al. | |
| 5,705,545 A | 1/1998 | Avar et al. | |

(Continued)

FOREIGN PATENT DOCUMENTS

DE 24 37 916 A 2/1976

(Continued)

OTHER PUBLICATIONS

S. D. Worley, F. Li, R. Wu, J. Kim, C.I. Wei, J.F. Williams, J.R. Owens, J.D. Wander, A.M. Bargmeyer, M.E. Shirtliff; "A Novel N-Halamine Monomer for Preparing Biocidal Polyurethane Coatings", Air Force Research Laboratory, Mar. 2002.*

(Continued)

*Primary Examiner* — Sean E Conley
(74) *Attorney, Agent, or Firm* — Chainey P. Singleton; Edwin S. Flores; Chalker Flores, LLP

(57) ABSTRACT

The present invention includes compositions, articles, methods controlling microbial contamination of a surface by functionalizing a surface of an object and binding one or more acyclic-amine structures to the surface. The one or more acyclic-amine structures are halogenated to form one or more acyclic N-halamine structures. The one or more acyclic N-halamine structures modulate the formation of a biofilm.

14 Claims, 7 Drawing Sheets

U.S. PATENT DOCUMENTS

| | | | |
|---|---|---|---|
| 5,714,127 | A | 2/1998 | DeWitt et al. |
| 5,817,806 | A | 10/1998 | Rossi et al. |
| 5,882,357 | A | 3/1999 | Sun et al. |
| 5,889,130 | A | 3/1999 | Worley et al. |
| 5,902,818 | A | 5/1999 | Worley et al. |
| 6,020,491 | A | 2/2000 | Wonley et al. |
| 6,077,319 | A | 6/2000 | Sun et al. |
| 6,162,452 | A | 12/2000 | Worley et al. |
| 6,241,783 | B1 | 6/2001 | Sun |
| 6,294,185 | B1 | 9/2001 | Worley et al. |
| 6,482,756 | B2 | 11/2002 | Li |
| 6,576,154 | B1 | 6/2003 | Li |
| 6,585,989 | B2 | 7/2003 | Herbst et al. |
| 6,670,412 | B1 | 12/2003 | Erderly et al. |
| 6,762,225 | B2 | 7/2004 | Malik et al. |
| 6,768,009 | B1 | 7/2004 | Sun et al. |
| 6,770,287 | B1 | 8/2004 | Sun et al. |
| 6,878,761 | B2 | 4/2005 | Gugumus |
| 6,969,769 | B2 | 11/2005 | Worley et al. |
| 7,084,208 | B2 | 8/2006 | Sun et al. |
| 7,335,373 | B2 | 2/2008 | Worley et al. |
| 7,358,373 | B2 | 4/2008 | Bamberg et al. |
| 2002/0123281 | A1 | 9/2002 | Wu |
| 2003/0056297 | A1 | 3/2003 | Sun |
| 2003/0143187 | A1 | 7/2003 | Worley et al. |
| 2004/0063831 | A1 | 4/2004 | Sheppard et al. |
| 2004/0086480 | A1 | 5/2004 | Worley et al. |
| 2004/0121681 | A1 | 6/2004 | Lindsay et al. |
| 2004/0127667 | A1 | 7/2004 | Worley et al. |
| 2004/0191315 | A1 | 9/2004 | Slattery et al. |
| 2004/0265565 | A1 | 12/2004 | Fischer et al. |
| 2005/0186173 | A1 | 8/2005 | Worley et al. |
| 2006/0148940 | A1 | 7/2006 | Sun et al. |
| 2007/0086976 | A1 | 4/2007 | Sun et al. |
| 2007/0092724 | A1 | 4/2007 | Li et al. |

FOREIGN PATENT DOCUMENTS

| | | |
|---|---|---|
| DE | 24 37 917 A | 2/1976 |
| EP | 02 40 370 A | 10/1987 |
| GB | 1211521 A | 11/1970 |
| WO | 96 08 949 A | 3/1996 |
| WO | 01/07550 A1 | 2/2001 |
| WO | 2002/006579 A2 | 1/2002 |
| WO | 2005/058814 A2 | 6/2005 |

OTHER PUBLICATIONS

Aggarwal, P., et al., "Development of an infection-resistant bifunctionalized Dacron biomateria," J Biomed Mater Res (2005), 75A:224-231.

Albert, M., et al., "Structure-Activity Relationships of Oligoguanidines-Influence of Counterion, Diamine, and Average Molecular Weight on Biocidal Activies," Biomacromolecules, (2003), 4:1811-1817.

Appendini, P., et al., "Review of antimicrobial food packaging," Innov. Food Sci. Emerg. Tech. (2002), 3:113-126.

Barker, J., et al., Effects of cleaning and disinfection in reducing the spread of Norovirus contamination via environmental surfaces, J Hosp Infect (2004), 58:42-49.

Binder, S., et al., "Emerging Infectious Diseases: Public Health Issues for the 21st Century," Science (1999), 284:1311-1313.

Chen, C. Z., et al., "Quaternary Ammonium Functionalized Poly(propylene imine) Dendrimers as Effective Antimicrobials: Structure-Activity Studies," Biomacromolecules, (2000), 1:473-480.

Eknoian, M. W., et al., "Monomeric and Polymeric N-Halamine Disinfectants," Ind. Eng. Chem. Res. (1998), 37:2873-2877.

Eknoian, M. W., et al., "Novel Antimicrobial N-halamine polymer coatings generated by emulsion polymerization," Polymer (1999), 40:1367-1371.

Jansson, A., et al., "Degradation of post-consumer polypropylene materials exposed to simulated recycling—mechanical properties," Polym. Degrad. Stab. (2003), 82:37-46.

Kruczala, K., et al., "Thermal Aging of Heterophasic Propylene-Ethylene Copolymers: Morphological Aspects Based on ESR, FTIR, and DSC," Macromolecules (2003), 36:1899-1908.

Kruczala, K., et al., "Thermal Aging of Heterophasic Propylene-Ethylene Copolymers: Spatial and Temporal Aspects of Degradation Based on ESR, ESR Imaging, and FTIR," Macromolecules (2003), 36:1909-1919.

Larson, M. A., et al., "Inactivation of *Bacillus subtilis* spores with ozone and monochloramine," Water Research (2003), 37:833-844.

Lee, H. J., et al., "Antibacterial effect of nanosized silver colloidal solution on textile fabrics," J Mater Sci (2003), 38:2199-2204.

Lee, S. B., et al., "Permanent, Nonleaching Antibacterial Surfaces. 1. Synthesis by Atom Transfer Radical Polymerization," Biomacromolecules, (2004), 5:877-882.

Motyakin, M. V., et al., "Spectral Profiling by 1D and 2D Electron Spin Resonance Imaging: Nitroxide Radicals in UV and Thermal Degradation of Poly(acrylonitrile-butadiene-styrene) Containing a Hindered Amine Stabilizer," Macromolecules (2001), 34:2854-2864.

Motyakin, M. V., et al., "Electron Spin Resonance Imaging and ATR-FTIR Study of Poly(acrylonitrile-butadienestyrene) Containing a Hindered Amine Stabilizer and Thermally Treated at 353 K," Macromolecules (2002), 35:3984-3992.

Muzzarelli, R. A. A., et al., "Fungistatic Activity of Modified Chitosans against *Saprolegnia parasitica*," Biomacromolecules, (2001); 2:165-169.

Neely, A. N., et al. "Survival of Enterococci and Staphylococci on Hospital Fabrics and Plastic," J Clin Microbiol (2000), 38:724-726.

Neely, A. N., et al., "Survival of Some Medically Important Fungi on Hospital Fabrics and Plastics," J Clin Microbiol (2001), 39:3360-3361.

Qian, L., et al., "Durable and Regenerable Antimicrobial Textiles: Improving Efficacy and Durability of Biocidal Functions," J Appl Polym Sci (2004), 91:2588-2593.

Rabea, E. I., et al., "Chitosan as Antimicrobial Agent: Applications and Mode of Action," Biomacromolecules, (2003), 4:1457-1465.

Setnescu, R., et al., "Chemiluminescence study on the oxidation of several polyolefins—I. Thermal-induced degradation of additive-free polyolefins," Polym. Degrad. Stab. (1998), 60:377-383.

Sun, G., et al., National Center Annual Report, NTC Project CO2-CD06 (Nov. 2002).

Sun, Y. et al. "Novel Refreshable N-Halamine Polymeric Biocides: Grafting Hydantoin-Containing Monomers onto High Performance Fibers by a Continuous Process," J. Appl. Polym. Sci. (2003), 88:1032-1039.

Sun, Y., et al., "Novel Refreshable N-Halamine Polymeric Biocides: N-Chlorination of Aromatic Polyamides," Ind Eng Chem Res (2004), 43:5015-5020.

Tennen, R., et al., "Mechanisms of killing of spores of *Bacillus subtilis* by iodine, glutaraldehyde and nitrous acid," J Appl Microbiol (2000), 89:330-338.

Tew, G. N., et al., "De novo design of biomimetic antimicrobial polymers," Proc. Natl. Acad. Sci. USA. (2002), 99:5110-5114.

Tiller, J. C., et al., "Designing Surfaces that Kill Bacteria on Contact," Proc. Natl. Acad. Sci. USA. (2001), 98:5981-5985.

International Search Report and Written Opinion for PCT/US2008/076687 dated Apr. 3, 2009.

Hahn, K., et al., "Chlorination of Substituted Polyacrylamides," Die Angewandte Makromolekulare Chemic (1976), 50:53-65.

International Search Report and Written Opinion for PCT/US2007/007506 dated Jul. 25, 2008.

Amornsakchai, T., et al. "Surface modification of low density polyethylene using accelerated decomposition of potassium persulfate and ceric ion induced acrylamide grafting." J Mater Sci Lett (2002), 21:1035-1038.

Braun, M. et al., "Antimicrobial polymers containing melamine derivatives. I. Preparation and characterization of chloromelamine-based cellulose." J Polym Sci Part A: Polym Chem (2004), 42:3818-3827.

Cen, L., et al., "Antibacterial activity of cloth functionalized with N-alkylated poly(4-vinylpyridine)." J Biomed Mater Res (2004),74A:70-80.

Chen, Z., et al., "N-Chloro-hindered amines as multifunctional polymer additives." Macromolecules (2005),38:8116-8119.

Depaola, L.G., et al., "A review of the science regarding dental unit waterlines." J Am Dent Assoc (2002),133:1199-1206.

Dhamodharan, R., et al., "Investigation of the mercat reaction as a tool for the introduction of nitrogen surface functionality on linear low-density polyethylene (LLDPE) and polypropylene (PP)." Langmuir (2001),17:3368-3374.

Gorman, S.P., et al., "The concomitant development of poly(vinyl chloride)-related biofilm and antimicrobial resistance in relation to ventilator-associated pneumonia." Biomaterials (2001),22:2741-2747.

Hall-Stoodley, L., et al., "Bacterial biofilms: from the natural environment to infectious diseases." Nature Rev Microbiol (2004),2:95-108.

Lin J., et al., "Antimicrobial treatment of nylon." J Appl Polym Sci (2001),81:943-947.

Lin J., et al., "Infrared characterization of biocidal nylon." Polymer (2001), 42:7903-7906.

Linger J.B., et al., "Evaluation of a hydrogen peroxide disinfectant for dental unit waterlines." J Am Dent Assoc (2001),132:1287-1291.

Luo J., et al., "Acyclic N-halamine-based fibrous materials: preparation, characterization, and biocidal functions." J Polym Sci: Part A Polym Chem (2006),44:3588-3600.

Mills S.E., "The dental unit waterline controversy: defusing the myths, defining the solutions." J Am Dent Assoc (2000),131:1427-1441.

Ozcan M., et al., "The effect of disinfectant agents in eliminating the contamination of dental unit water." J Oral Rehabili (2003),30:290-294.

Ramage G., et al., "Formation of Propionibacterium acnes biofilms on orthopaedic biomaterials and their susceptibility to antimicrobials." Biomaterials (2003),24:3221-3227.

Roberts H.W., et al., "Dental unit waterline antimicrobial agent: effect on dentin bond strength." J Am Dent Assoc (2000),131:179-183.

Sun G., et al., "Durable and regenerable antibacterial finishing of fabrics with a new hydantoin derivative." Ind Eng Chem Res (2001),40:1016-1021.

Sun Y., et al., "Novel refreshable N-halamine polymeric biocides containing imidazolidin-4-one derivatives." J Polym Sci: Part A (2001),39:3073-3084.

Sun Y., et al., "Durable and regenerable antimicrobial textile materials prepared by a continuous grafting process." J Appl Polym Sci (2002),84:1592-1599.

Sun Y., et al., "Synthesis, characterization, and antibacterial activities of novel N-halamine polymer beads prepared by suspension copolymerization." Macromolecules (2002), 35:8909-8912.

Tao G., et al., "Surface functionalized polypropylene: Synthesis, characterization, and adhesion properties." Macromolecules (2001),34:7672-7679.

Walker J.T., et al., "Microbiological evaluation of a range of disinfectant products to control mixed-species biofilm contamination in a laboratory model of a dental unit water system." Appl Environ Microbiol (2003),69:3327-3332.

Yorganci K., et al., "Activity of antibacterial impregnated central venous catheters against Klebsiella pneumoniae." Intensive Care Med (2002),28:438-442.

* cited by examiner

N-HALAMINE-BASED RECHARGEABLE BIOFILM-CONTROLLING TUBULAR DEVICES, METHOD OF MAKING AND USING

CROSS-REFERENCE TO RELATED APPLICATIONS

This application claims priority to U.S. Provisional Application Ser. No. 60/908,168, filed Mar. 26, 2007, the contents of which is incorporated by reference herein in its entirety. This application is a related to U.S. Provisional Patent Application Ser. No. 60/707,331, filed Aug. 11, 2005, and U.S. patent application Ser. No. 11/324,616, filed Jan. 3, 2006, which claims priority to U.S. Provisional Patent Application Ser. No. 60/640,985, filed Jan. 3, 2005, the contents of each of which are incorporated by reference herein in their entireties. This application is also related to U.S. patent application Ser. No. 11/389,968, filed Mar. 27, 2006 and U.S. Provisional Patent Application Ser. No. 11/502,892, filed Aug. 11, 2006, the contents of each of which are incorporated by reference herein in their entireties.

STATEMENT OF FEDERALLY FUNDED RESEARCH

This invention was made with U.S. Government support under Contract No. 5R21 DE016403 awarded by the NIH/NIDCR. The government has certain rights in this invention.

TECHNICAL FIELD OF THE INVENTION

The present invention relates in general to the field of N-halamine-based rechargeable biofilm-controlling devices.

BACKGROUND OF THE INVENTION

Without limiting the scope of the invention, its background is described in connection with N-halamine-based rechargeable biofilm-controlling devices. Contamination of materials by microorganisms (e.g., bacteria, fungi, and/or protozoa, with associated bacteriophages and other viruses) is of great concern in the many areas, and in particular to the health care industry where patients are already in a weaken state or are more susceptible to these organisms. It is well known that these microorganisms can survival of on various materials and even transferred between materials, surfaces, animals and humans.

These microorganisms can further accumulate and become embedded in a polysaccharide matrix to form a biofilm that adheres to surfaces (e.g., solid biologic and/or non-biologic surface). Given the unique structure of a biofilm it is not uncommon for microorganisms to express new and sometimes more virulent phenotypes when grown within a biofilm. In addition, microorganisms within biofilms have increased resistance to antimicrobial compounds, even though these same microorganisms are sensitive to these agents if grown under planktonic conditions.

Furthermore, the structure and characteristics of biofilms allow the growth and proliferation of contaminants and result in antimicrobials being readily inactivated or fail to penetrate into the biofilm making the cleaning and removal of pathogenic bacteria, molds, fungi and viruses extremely difficult. The biofilms increase the opportunity for gene transfer between/among microorganisms allowing microorganisms resistant to antimicrobials or chemical biocides to transfer the genes for resistance to neighboring susceptible microorganisms. Gene transfer can convert a previous a virulent commensal organism into a highly virulent pathogen.

The interface between fluids and surfaces has the potential for biofilm development. The turbulent fluid flow over the surface does not provide protection from biofilm development, as evident by biofilm formation in water cooling towers for air conditioners, municipal water storage tanks, private wells, drip irrigation systems and industrial fluid processing operations.

The removal/prevention of biofilms is further complicate in fluid baths, circulating systems and water systems, especially in medical and dental devices were any treatment or agents used to impair biofilm formation must be safe to the patient. The anti-biofilm agent must furthermore not interfere with the characteristics (e.g., manipulability, softness, water-tightness, tensile strength or compressive durability) of a medical device.

Consequently, the formation of biofilms on medical/dental devices, medical implants, artificial organs, catheters, ventilators and dental unit waterline tubes has caused serious consequences. For example, biofilms have been seen on dental unit waterline tubing as far back as 1963. The low flow rate and frequent quiescent periods make the inner surfaces of dental unit waterline tubing are a particularly favorable environment for development of biofilms. Plastic materials used in DUWL such as polypropylene (PP), polyethylene (PE), and polyurethane (PU) are excellent substrates for microbial adhesion and the subsequent proliferation of biofilms. Once formed, DUWL biofilms are very difficult to destroy, and often have caused serious concerns and clinical problems. For example, during dental operations, although the biofilm remains fixed to the tubing wall, microbes in the biofilm can be continuously dislodged into the treatment water, resulting in high microbial counts and a hazard for dental personnel who inhale the aerosolized particles and a health concern for patients who are treated with water.

To treat this problem approaches currently used in the industry include the use of independent water systems, intermittent or continuous chemical treatments, point-of-use filters, sterilizations of water delivery systems, etc. However, none of these methods could completely prevent the formation of biofilms and high microbial counts in DUWLs continue to be concerns in general practice.

The foregoing problems have been recognized for many years and while numerous solutions have been proposed, none of them adequately address all of the problems in a single device, e.g., effectiveness against many forms of bacteria, toxicity, stability and rechargeability.

SUMMARY OF THE INVENTION

The present inventors recognized that the formation of biofilms on tubing, pipes and other surfaces are serious problems in many industries, e.g., medical, dental, environmental applications and industrial applications. The present inventors recognized a need for a surface coating/derivatization bactericidal and a method of using and making it that would be applicable to most tubing to prevent biofilm formation.

The present inventors recognized that N-halamine based tubing and pipes may be used to control the formation of biofilms on these surfaces. The present inventors recognized that N-halamines and/or their precursors are covalently bound to, mixed with, coated or painted onto tubing and. pipe materials. The new tubing aid pipes can effectively control the fobation of biofilms on the surfaces. The present invention provides many useful applications in medical, dental, environmental and industrial applications.

The present invention provides a surface of polypropylene (PP) tubing were hydroxylated with potassium persulfate. The resultant tubing surfaces were grafted with methacrylamide (MAA) using ceric (IV) ammonium nitrate (CAN) as an initiator. Upon chlorination treatment with diluted chlorine bleach, some of the amide groups in the grafted MAA side chains are transformed into stable acyclic N-halamines. The chlorinated MAA-grafted tubing provides a potent and rechargeable biofilm-controlling functions against the test microorganisms.

Specifically the present invention provides acyclic N-halamine structures covalently bound onto the inner walls of polypropylene (PP) tubes by a surface funtionalization treatment. The N-halamine-based tubes effectively prevented the initial adhesion of *P. aeruginosa*. An in vitro continuous flowing model was used to evaluate the biofilm-controlling functions of the samples.

The present invention provides a method of controlling microbial contamination of a tubing surface. At least a portion of an inner surface of a tube is functionalized and one or more methacrylamides are bound to the inner surface. The one or more methacrylamides are halogenated to form one or more acyclic N-halamines. The one or more acyclic N-halamines modulate the growth of a biofilm on the inner surface of the tube.

The present invention also provides a method of controlling microbial contamination of a surface by functionalizing a surface of an object and binding one or more acyclic-amine structures to the surface. The one or more acyclic-amine structures are halogenated to form one or more acyclic N-halamine structures. The one or more acyclic N-halamine structures modulates the formation of a biofilm.

A biofilm resistant surface is provided by the present invention and includes a surface and one or more acyclic-amines immobilized to the surface by a covalent bond to form a biofilm resistant surface. The present invention also provides a biofilm resistant conduit comprising one or more acyclic N-halamines immobilized to at lease a portion of an inner surface of at least a portion of a conduit, wherein the one or more acyclic N-halamines modulate the formation of a biofilm on the conduit.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
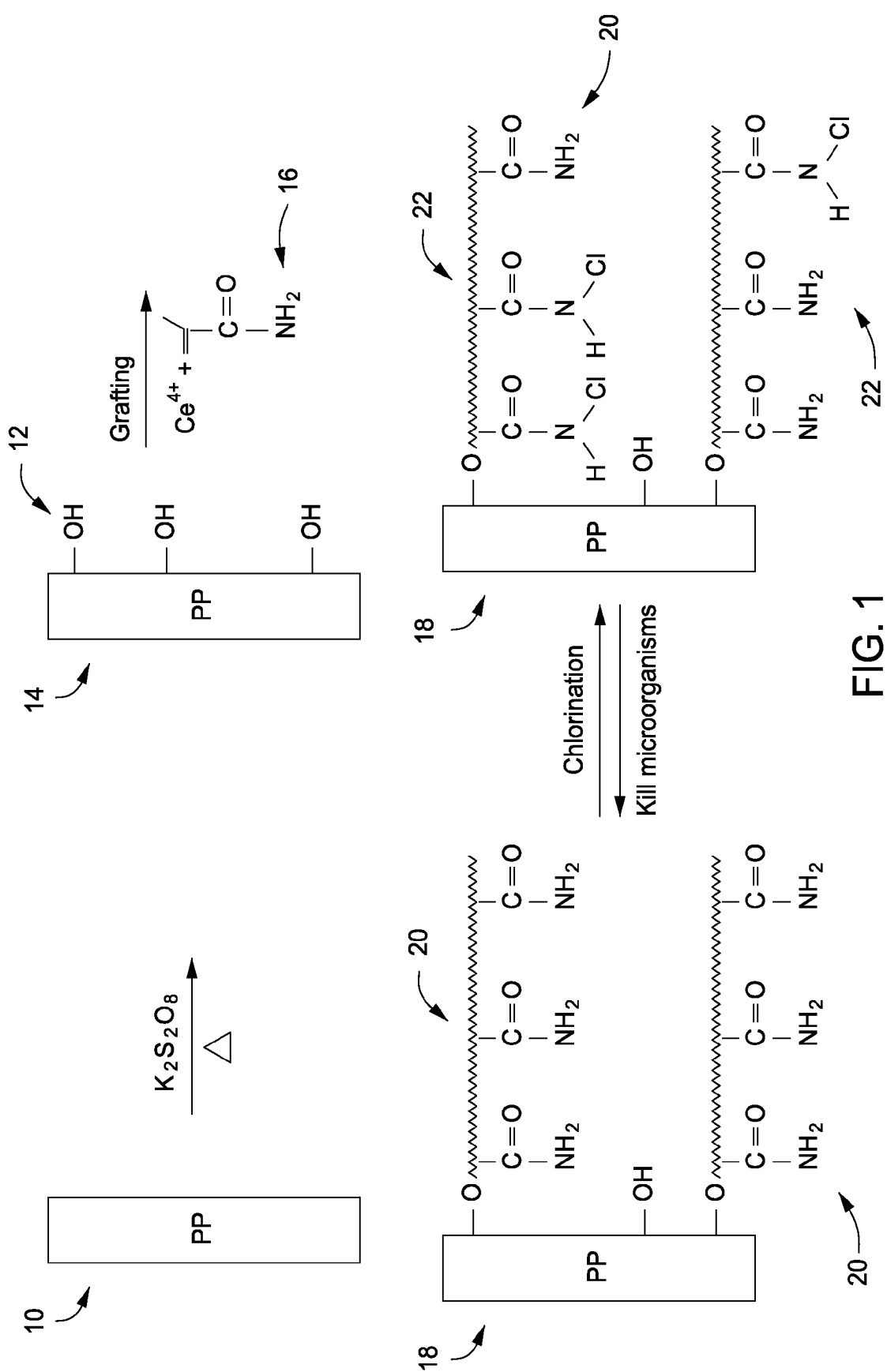
FIG. 1 is a scheme of one of the preparation pathway of the chlorinated-MAA-grafted-OH-PP tubes.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "antimicrobial compound," "antimicrobial," "microbicidal," "biocide," "biocidal" and "halogenated amide antimicrobial" are used interchangeably herein and refer to halogenated amides that function as biocides to kill at least some types of microorganisms, or to inhibit the growth or reproduction of at least some types of microorganisms (i.e., compounds which inhibit the growth of, or kills, microorganisms such as bacteria, molds, slimes, fungi, etc.).

As used herein, the term "alkyl" denotes branched or unbranched hydrocarbon chains, preferably having about 1 to about 10 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

As used herein, the term "alkylene" refers to a divalent alkyl group as defined above, such as methylene (—$CH_2$—), propylene (—$CH_2CH_2CH_2$—), chloroethylene (—CHCl$CH_2$—), 2-thiobutene (—$CH_2$CH(SH)$CH_2CH_2$), 1-bromo-3-hydroxyl-4-methylpentene (—CHBr$CH_2$CH(OH)CH($CH_3$)$CH_2$—), and the like.

As used herein, the term "alkenyl" denotes branched or unbranched hydrocarbon chains containing one or more carbon-carbon double bonds.

As used herein, the term "alkynyl" refers to branched or unbranched hydrocarbon chains containing one or more carbon-carbon triple bonds.

As used herein, the term "aryl" denotes a chain of carbon atoms which form at least one aromatic ring having between about 4-50 carbon atoms, such as phenyl, naphthyl, triazine, naphthalene, Anthracene, Anthraquinone and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

As used herein, the term "alkoxy" denotes —OR—, wherein R is alkyl. The term "alkylcarbonyl" denote an alkyl group as defined above substituted with a C(O) group, for example, $CH_3C(O)$—, $CH_3CH_2C(O)$—, etc. As used herein, the term "alkylcarboxyl" denote an alkyl group as defined above substituted with a —C(O)O group, for example, $CH_3C(O)O$—, $CH_3CH_2C(O)O$—, etc. As used herein, the term "amido" denotes an amide linkage: —C(O)NHR (wherein R is hydrogen or alkyl). The term "amino" denotes an amine linkage: —NR—, wherein R is hydrogen or alkyl. The term "carbocycle" means a cyclic hydrocarbon chain having about 4 to about 8 ring carbons such as cyclopentyl, cyclohexyl, etc. These groups can be optionally substituted with one or more functional groups as defined under "alkyl" above.

As used herein, the term "carboxyl" denotes —C(O)O—, and the term "carbonyl" denotes —C(O)—. The term "cycloalkyl" signifies a saturated, cyclic hydrocarbon group with 3-8, i.e. cyclopropyl, cyclobutyl, cyclopentyl and cyclohexyl and the like.

As used herein, the terms "N-halamine dye," "Heterocyclic N-halamine dye," "cyclic N-halamine dye" and "N-halamine pigments" denotes a class of chemicals that contain a halogen bound to a nitrogen atom, where the nitrogen is a member of a ring, along with carbon atoms or in communication (e.g., bound to the ring) with the ring. When bound to the nitrogen, the halogen is in a stable form and retains the ability to interact with targets on the surfaces of bacteria and other microbes. The presence of the halogen renders it biocidal. For example, heterocyclic, monocyclic compounds having 4 to 8 membered ring, wherein at least 3 members of the ring are carbon, and from 1 to 3 members of the ring are nitrogen heteroatom, and from 0 to 1 member of the ring is oxygen heteroatom. Additionally, there may be from 0 to 3 carbon members comprise a carbonyl group, and wherein at least 1 to 3 nitrogen atoms are substituted with a hydroxyalkyl group, such as —$CH_2$ OH, or an alkoxyalkyl group, such as —$CH_2OCH_3$. In addition, the ring members can be further substituted with alkyl groups, such as methyl, ethyl, etc.

The term "halogen" includes chlorine, fluorine, bromine, iodine and mixtures thereof. As used throughout the specification halogens may be used interchangeably. Although specific figures are represented with a specific halogen, the skilled artisan will clearly understand that the halogen may be substituted with other halogens. As used herein, the specific halogen or general halogen group X may be chlorine, fluorine, bromine, or iodine and not intended to limit the specific molecule to only a single halogen. The general halogen group is denoted herein by X and in some instances $X_2$ which denotes 2 halogens that may be independently a chlorine, a fluorine, a bromine, or an iodine.

The term "heteroaryl" refers to an aromatic monocyclic or bicyclic radical having 5 to 10, preferably 5 to 6 ring atoms, containing one to three heteroatoms, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, pyridinyl, isoxazolyl or thiazolyl. Optionally, the heteroaryl group can be mono-substituted, di-substituted or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl. In addition, the compound may have one or more heteroaryl or Polycyclics attached to the base structure.

As used herein the term "Polycyclics" denotes organic compounds that are molecules containing two or more simple aromatic rings fused together by sharing two neighboring carbon atoms. Examples are naphthalene, anthracene and phenanthrene. In addition, the present invention may include one or more substituted aromatics. Many chemical compounds contain simple aromatic rings in their structure. For example, pyrrole, or pyrrol, is a heterocyclic aromatic organic compound having five-membered ring with the formula $C_4H_4NH$. Pyridine is a chemical compound with the formula $C_5H_5NH$ and in addition substituted derivatives may also called pyrroles. In addition some of the molecules of the present invention may have one or more imide functional groups that include two carbonyl groups bound to a primary amine or ammonia, for example, phthalimide. They may be either simple aromatic rings or non-aromatic rings. Some examples are pyridine, pyrimidine, triazine, dioxane, pyridine, imidazole, pyrazole, oxazole, thiophene, and their benzannulated analogs (e.g., benzimidazole).

The term "heterocycle" means a straight chain or ring system that may contain from zero to four heteroatoms selected from N, O and S, wherein the nitrogen and sulfur atoms are optionally oxidized and the nitrogen atom(s) may be optionally quaternized. These groups can be themselves be optionally substituted with one or more functional groups as defined above.

As used herein, the terms, "polymer" and "copolymer" are at times used interchangeably to mean a cyclic amine or N-halamine unit joined by a linkage to a second cyclic amine or N-halamine unit is not meant to be limiting as to the number of cyclic amine or N-halamine units in a polymer, e.g., two or more cyclic amine or N-halamine units, and the number of units in any given polymer can vary according to the use intended for the polymer. Other polymers include flexible PVC, polyurethanes, polyolefins, thermoplastic polyolefins, thermoplastic elastomers, rubber, silicones, polyester; however, the skilled artisan will recognize other polymers may be used. The polymer may be a random copolymer contains a random arrangement of the multiple monomers. The polymer may be a block copolymer contains blocks of monomers of the same type. The polymer may also be a graft copolymer contains a main chain polymer consisting of one type of monomer with branches made up of other monomers. For example, the polymer can comprise 2, 3, 4, 5, 6, 7, 8, 9, 10, 20, 25, 30, 40, 50, 75, 100, 150, 200, 250, 500, 1000 units, or more.

An N-halamine is a compound containing one or more nitrogen-halogen covalent bonds that is normally formed by the chlorination or bormination of imide, amide, or amine groups. One property of N-halamines is that when microbes come into contact with the N—X structures (X is Cl or Br), a halogen exchange reaction occurs, resulting in the expiration of the microorganisms. This process consumes halogens, but the consumed halogens can be fully recharged by another halogen treatment. Thus, N-halamines are generally regarded as rechargeable batteries of covalently bound halogens. The N-halamine antimicrobial materials may contain aliphatic, cyclic and/or alicyclic structures to ensure the stability of the nitrogen-halogen covalent bond.

More particularly, a method and composition are provided that include a class of methacrylamide (MAA)-based biocidal materials. MAA is polymerized to form its homopolymer, polymethacrylamide (PMAA), MAA is copolymerized with other polymerizable monomers to form copolymers or MAA is bound to other polymeric materials or surfaces with or without the presence of other monomers. The resultant MAA-based polymers can be used alone or blended/mixed with other materials for binding to another material. Upon exposure to halogen source(s), acyclic N-halamines are formed in the MAA-based materials, which can provide durable and rechargeable biocidal effects against biofilms, bacteria, spores, fungi, yeasts, and virus.

The N-halamine compounds of the present invention include aromatic, cyclic and acyclic compounds. The acyclic N-halamine compounds of the present invention include aliphatic compounds that are non-aromatic organic compounds and have a general open chain hydrocarbon structure, e.g., not only fatty acids and other derivatives of the paraffin hydrocarbons (alkane), but also unsaturated compounds, such as the ethylene (alkene) and acetylene (alkyne) series. The number of molecules in the chain may vary depending on the application and the compound may be branched or unbranched. In addition, compounds may contain modifications, side groups, substitutions and modifications that will be known to the skilled artisan.

The present invention includes a rechargeable acyclic N-halamine polymer. The rechargeable acyclic N-halamine polymer includes an aliphatic N-halamine compound bound to a surface and one or more halides associated with the aliphatic N-halamine compound. The one or more halides provided inactivation of bacteria cells, spores, fungus, yeasts, viruses or a combination thereof. In one example, the acyclic N-halamine compound is a methacrylamide polymer; however, other polymers may be used to form the acyclic N-halamine compound. In addition, the acyclic N-halamine compound may be constructed from a variety of monomers of similar or different types and combinations to produce a polymeric material.

In addition, the present invention is rechargeable by contacting the aliphatic N-halamine grafted polymer with a halide source to recharged the aliphatic N-halamine compound. Thus once the aliphatic N-halamine grafted polymer has lost at least part of the microbial activity it can be replaced or recharged to again inactivate biofilms, bacteria cells, spores, fungus, yeasts, viruses or a combination thereof.

The present invention provides a method of controlling microbial contamination of a tubing surface. At least a portion of an inner surface of a tube is functionalized and one or more methacrylamides are bound to the inner surface. The one or more methacrylamides are halogenated to form one or more acyclic N-halamines. The one or more acyclic N-halamines modulate the growth of a biofilm on the inner surface of the tube.

One embodiment of the present invention provides the modulation of growth of a biofilm on the inner surface of a tube. Other embodiments include other surfaces including a wall, a bottom or the sides of a container; a heater or heating coil; a chiller or chilling coil; a plate, a filter a grid, or a grate; a bath, or other storage container; a pipe, a channel, a groove, valley, aqueduct or a conduit. The one or more acyclic N-halamines may be placed on the entire surface, part of the surface or layered on the surface.

Microbial biofilms are defined as populations of microorganisms that are concentrated at an interface (e.g., usually a solid-liquid interface) and typically surrounded by a matrix of extracellular polymeric substance.[1] Biofilms are formed through the adhesion of bacteria to the solid surface, followed by growth-dependent accumulation of cells, which generates bacteria cell clusters that anchor tightly to the surfaces.[1-3] The most troubling characteristic of microbes embedded in biofilms is their superior resistance to disinfection. For example, bacteria living in a biofilm may be up to 1000 times more resistant to biocides than free-floating bacteria. This high resistance is believed to be induced by the combined action of many factors, including binding of the agent, a lack of penetration of inhibitors, the localization of neutralizing enzymes, and the expression of a resistant phenotype due to surface growth.[4,5] Consequently, the formation of biofilms on medical/dental devices, medical implants, artificial organs, catheters, ventilators and dental unit waterline tubes has caused serious consequences.

The presence of biofilms on dental unit waterline (DUWL) tubing was first reported in 1963,[6] and this report has been repeatedly confirmed by subsequent investigations.[7-17] It is generally accepted that because of the low flow rates and frequent quiescent periods, the inner surfaces of DUWL tubing are a particularly favorable environment for development of biofilms. Plastic materials used in DUWL such as polypropylene (PP), polyethylene (PE), and polyurethane (PU) are excellent substrates for microbial adhesion and the subsequent proliferation of biofilms. Once formed, DUWL biofilms are very difficult to destroy, and they have caused serious concerns and health issues.

For example, it has been reported that the toxic by-products produced by biofilm bacteria may cause clinical problems.[7] More importantly, during dental operations, although the biofilm remains fixed to the tubing wall, microbes in the biofilm can be continuously dislodged into the treatment water, resulting in high microbial counts (e.g., 1,000 to 160 million CFU/mL) in DUWLs.[7-9] Therefore, DUWL biofilm is both an occupational hazard for dental personnel who inhale the aerosolized particles and a health concern for patients who are treated with water that does not meet the Environmental Protection Agency (EPA) Safe Drinking Water Standard.[6-11]

In response to the increasing concern of the potential health consequences associated with high microbial counts in dental treatment water caused by DUWL biofilms, the American Dental Association set a goal of no more than 200 CFU/mL of heterotrophic, mesophilic bacteria in unfiltered output water.[10,11] Accordingly, significant efforts have been made to control biofilms and improve dental water qualities. Current approaches include the use of independent water systems, intermittent or continuous chemical treatments, point-of-use filters, sterilizations of water delivery systems, etc.[12-7] However, none of these methods could completely prevent the formation of biofilms, and high microbial counts in DUWLs continue to be concerns in general practice.

The present inventors recognized that covalently bound N-halamine structures onto tubing surfaces would provide potent and rechargeable biofilm-controlling functions. N-halamines are compounds containing one or more nitrogen-halogen covalent bonds that are normally formed by the chlorination or bromination of imide, amide, or amine groups. N-halamines have excellent biocidal functions against a wide range of microorganisms including bacteria, viruses, fungi, and spores, making them attractive candidates for water treatment[18-20] and biocidal functional modifications of textiles and polymeric materials.[21-28]

The present invention grafts methacrylamide (MAA) onto PP tubes, one of the most widely used tubing materials in DUWLs. After chlorine bleach treatment, part of the amide groups of the grafted MAA side chains were transformed into acyclic N-halamines. The biofilm-controlling functions of the inner surfaces of the resultant tubes were tested with continuous flow of $10^3$-$10^4$ CFU/mL of *Pseudomonas aeruginosa* (*P. aeruginosa*), one of the most cited gram-negative water bacteria that are responsible for DUWL biofilms.[7,29]

For example, isotactic polypropylene (hereafter referred to as PP) tubes (e.g., I.D.: 3/16 inch) were obtained from Nalge Nunc International Corporation (Rochester, N.Y.). The tubes were extracted with refluxing acetone for 4 hours to remove surface contaminants and possible impurities. Cerium (IV) ammonium nitrate (CAN) and methacrylamide (MAA) were provided by VWR International, Inc. (West Chester, Pa.). MAA was purified by recrystallization from distilled water before use. Potassium persulfate was purchased from Fisher Chemicals (Fair Lawn, N.J.).

The present invention uses a functional modification method developed by Bamford and Al-Lamee[30] to introduce hydroxyl groups onto tube surfaces. For example, PP tubes were treated with an aqueous solution containing about 20 wt % of potassium persulfate at 80° C. for hours 30 hours under $N_2$ atmosphere. At the end of the reaction, the tubes were taken out of the solution, washed thoroughly with distilled water, and dried at 60° C. until they reached a constant weight.

Grafting MAA onto the hydroxylated PP tubes (MAA-grafted-OH-PP tubes). The hydroxylated PP tubes were grafted with MAA using CAN as the initiator.[30] For example, 10 grams of the OH-PP tubes were immersed in 400 mL distilled water containing 0.04 mol/L of nitric acid and 0.004 mol/L of CAN under $N_2$ atmosphere. The initiator was allowed to react with the OH-PP tubes for 30 minutes. After this treatment, MAA was added into the reacting solution (e.g., MAA concentration: 10 wt %). The solution was stirred at 50° C. for 5 hours. At the end of the reaction, the grafted tubes were removed, washed thoroughly with distilled water at between about 60° C. and about 70° C. (e.g., 5×400 mL; 30 min for each treatment) and sonicated at room temperature for 30 minutes to remove possible homopolymers and un-reacted MAA. The resultant tubes were dried at about 60° C. to reach constant weights.

Preparation and characterization of the chlorinated-MAA-grafted-OH-PP tubes. PP is widely used as tubing materials in DUWLs and in other medical, industrial, and environmental settings because of its excellent physical and chemical stability, good processability, and low cost. However, tubing and other devices made from PP are susceptible to microbial adhesion, colonization, and biofilm formation.

The present invention provides a functionally modified PP tubing surfaces to introduce N-halamines into the chemical structures to control biofilms. PP surface functionalization has been the subject of a number of studies.[36-41] The present invention uses ceric ion-induced surface grafting, which is particularly attractive because it is easy to conduct and does not require any special equipment.[30,42] Although, other methods of surface grafting may also be used.

FIG. 1 illustrates a preparation pathway of the chlorinated-MAA-grafted-OH-PP tubes. In the first step, the PP tubes 10 were treated with potassium persulfate ($K_2S_2O_8$) under $N_2$ atmosphere, which abstracted hydrogen atoms from PP,[30] creating hydroxyl groups 12 on the tubing surfaces (OH-PP) 10. In the second step, the OH-PP tubes 14 reacted with CAN and MAA 16. The Ce (IV) ions could form intermediate coordination complexes with OH-PP 14,[43] which disproportionated unimolecularly, forming cerous ions and PP macro-free radicals that initiated the grafting polymerizations of MAA 20 onto the tubing surfaces (MAA-grafted-OH-PP tubes) 18. In the final step, the inner surfaces of the MAA-grafted-OH-PP tubes 18 were chlorinated through the treatment with a diluted chlorine bleach. During this process, some of the amide groups in the grafted MAA side chains 20 were transformed into acyclic N-halamines 22, which provided biofilm-controlling functions.

Figure 2:
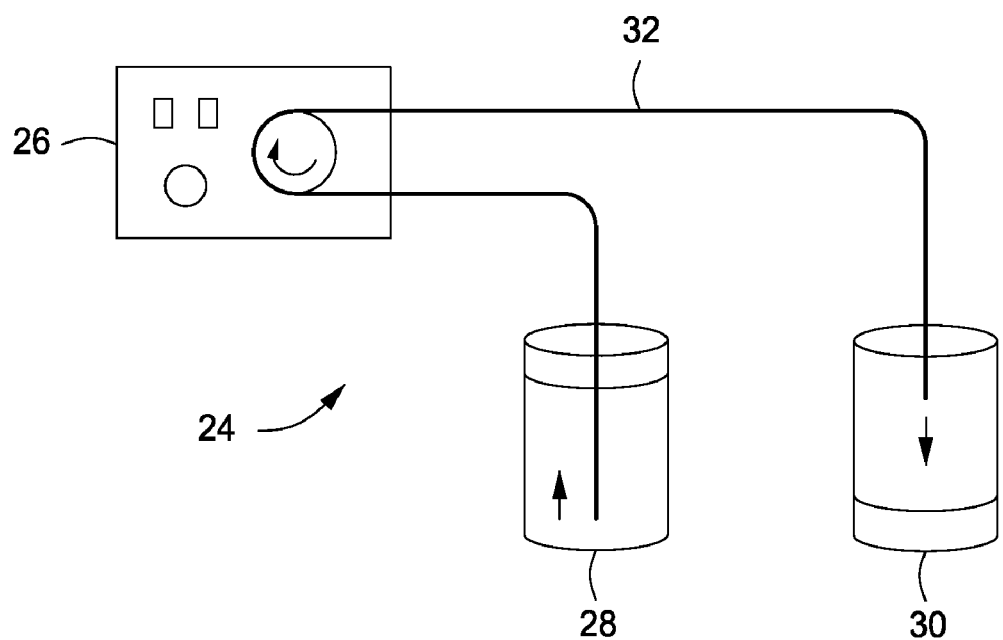
FIG. 2 is a schematic of one device for chlorinating the inner surfaces of the tube sample.

FIG. 2 is a schematic of the experimental setup for chlorinating the inner surfaces of the tube samples. The chlorination device 24 includes a pump device 26 attached to a fluid input 28 and a fluid collection 30 through the tubing 32. The pump device 26 moves the fluid through the tubing 32 from the fluid input 28 to the fluid collection 30.

The inner surfaces of the MAA-grafted-OH-PP tubes were chlorinated using a variable-speed mini pump (Control Company, Friendswood, Tex.), as shown in FIG. 2. In this treatment, the input fluid (e.g., 0.6 wt % of sodium hypochlorite solution containing 0.005 wt % of Triton X-100) flowed through the MAA-grafted-OH-PP tubes at room temperature for 2 hours. The pH value of the flowing solution was adjusted to pH 4, and the flow rate was kept at 4.0-4.5 mL/min. After chlorination, the input fluid was changed to distilled water, which flowed through the tubes for 1 hour at 4.0-4.5 mL/min to remove any residual free chlorine (e.g., the washing water was tested with KI/starch to ensure that most of the free chlorines were washed away). The resultant tubes were dried in a vacuum oven at room temperature for 6 hours and stored in a desiccator under reduced pressure for 72 hours to reach constant weights.

The active chlorine contents of the inner walls of the chlorinated MAA-grafted-OH-PP tubes were determined by iodimetric titration using a method reported previously.[26] Briefly, a 1-cm section (e.g., the inner surface area was 1.5 cm$^2$) of the N-halamine-based PP tubes were cut into small pieces, which were treated with 1 g KI in 40 mL of distilled water containing 0.005 wt % of Triton X-100 at room temperature under constant stirring for 60 minutes. The formed $I_2$ was titrated by 0.001 mol/L of standardized sodium thiosulfate aqueous solution. The same length of un-chlorinated MAA-grafted-OH-PP tube sample was also titrated using the same method as controls. Available active chlorine content on the chlorinated MAA-grafted-OH-PP tubes was calculated according to Equation 1:

$$[Cl] = \frac{35.5}{2} \times \frac{(V_{cl} - V_0)}{S_{cl}} \times 10^6 \quad (1)$$

where [Cl] was the active chlorine content (μg/cm$^2$), $V_{Cl}$ and $V_0$ were the volume (mL) of sodium thiosulfate solutions consumed in the titration of the chlorinated and un-chlorinated samples, respectively; and $S_{Cl}$ was the inner surface area of the chlorinated tubing sample (cm$^2$). Each test was repeated 3 times.

Biofilm-controlling functions of the chlorinated MAA-grafted OH-PP tubes. *P. aeruginosa* (ATCC 10145) was purchased from American Type Culture Collection (ATCC, Manassas, Va.). In the microbial studies, the bacteria were grown in nutrient broth at 37° C. for 24 h. The bacterial suspensions were centrifuged, washed with sterile phosphate buffered saline (PBS), and then resuspended in PBS to predetermined densities (colony forming units per milliliter, or CFU/mL).[31] To ensure lab safety, all the microbial studies followed the guidelines provided by the U.S. Department of Health and Human Services.[32]

To test the initial adhesion of bacteria onto the tubing samples, a series of 1-cm sections of the original PP tubes, un-chlorinated MAA-grafted-OH-PP tubes, and chlorinated MAA-grafted-OH-PP tubes were immersed individually in vials containing 1 mL of $10^6$-$10^7$ CFU/mL of *P. aeruginosa* suspension in PBS. The vials were shaken gently at 37° C. for 1 hour in a water bath. After shaking, each section was taken out of the bacterial suspension with sterile forceps, and gently washed 3 times with sterile PBS to remove any non-adherent bacteria. Half of the washed tubing sections were sonicated individually for 20 minutes using an Ultrasonic cleaner (Branson 1510) and then vortexed for 60 seconds to transfer the adherent bacteria into sterile PBS. This treatment could detach most of the cells without affecting microbial growth.

The resultant solution was serially diluted, and 100 μl of each diluent were placed onto nutrient agar plates in duplicates. After overnight incubation at 37° C., the colony forming units on each agar plate were counted, the level of adherent bacteria on each tubing section was calculated, and the results were presented as $CFU/cm^2$.[3,4,33,34] Each test was repeated 3 times.

At the same time, the other half of the washed tubing sections were fixed in 2.5% of glutaraldehyde in 0.1 M sodium cacodylate buffer and stored at 4° C. overnight. At the end of the fixation, the samples were washed 3 times with PBS, followed by step dehydration with 25%, 50%, 70%, 95%, and 100% ethanol (10 min at each concentration).[35] The resultant samples were then dried, the inner walls were sputter coated with silver and observed with a LEO 1530 SEM.

In vitro biofilm-controlling activity, an in vitro continuous flowing model was developed to simulate the real DUWL working conditions to evaluate the biofilm-controlling functions of the chlorinated MAA-grafted-OH-PP tubes. In the biofilm-controlling study, about $10^3$-$10^4$ CFU/mL of *P. aeruginosa* suspension in sterile distilled water (the water was buffered with a 1:100 dilution of sterile PBS to minimize the possibility of incidentally lysing the challenge organisms owing to change in osmotic pressure) was prepared, which was pumped through the chlorinated MAA-grafted-OH-PP tubes at room temperature. On weekdays, everyday the bacteria flow was continued for 8 hours at a rate of about 4.0-4.5 mL/min. At nights and on weekends, the pump was shut off and the bacteria solution was changed weekly. At different periods of flowing, a series of 1-cm sections were cut from the tubing end, which were gently washed 3 times with PBS. Half of the sections were sonicated and votexed to determine the level of recoverable adherent bacteria, and the other half was subjected to SEM observations, using the same procedures as described above. The biofilm-controlling study continued for 4 weeks. The original PP tubes and un-chlorinated MAA-grafted-OH-PP tubes were tested under the same conditions as controls and each test was repeated 3 times.

Rechargeability of the biofilm-controlling activity. After a period of bacteria solution flowing, the pump was shut off and the bacterial solution was changed to diluted chlorine bleach. The chlorinated-MAA-grafted-OH-PP (the sample) tubing and the original PP tubing (the control) were re-chlorinated with diluted bleach, following the same procedure as described herein. The biofilms-controlling functions of the re-chlorinated control and sample tubes were reevaluated using the same methods as described above. The re-chlorinating and reevaluating processes were repeated 3 times.

FIGS. 3A-3D are attenuated total reflection Fourier transform infrared spectra (hereafter referred to as ATR) of treated and untreated surfaces to examine the surface functionalization reactions. ATR spectra of the samples were recorded on a Thermo Nicolet Avatar 370 FT-IR spectrometer with ATR accessory (Woburn, Mass.).

FIG. 3A is an ATR spectrum of the surface of the original PP tube. In the spectrum of original PP (FIG. 3A), the peaks around 2900 $cm^{-1}$ are caused by —$CH_2$ stretching, and the absorption bands at 1465 $cm^{-1}$ and 1373 $cm^{-1}$ are related to =$CH_2$ and —$CH_3$ bending of PP, respectively.[39] FIG. 3B is an ATR spectrum of the surface of the OH-PP tube. After treatment with $K_2S_2O_8$, a broad peak centered at 3450 $cm^{-1}$ can be observed (FIG. 3B), which is attributable to the stretching vibration of the newly created hydroxyl groups on the surfaces of the hydroxylated PP. FIG. 3C is an ATR spectrum of the surface of the MAA-grafted-OH-PP tube. In the spectrum of MAA-grafted-OH-PP (FIG. 3C), the amide I and amide II bands appear at 1660 $cm^{-1}$ and 1600 $cm^{-1}$, respectively, 44 suggesting that MAA is successfully grafted onto the tube surfaces. FIG. 3D is an ATR spectrum of the surface of a chlorinated MAA-grafted-OH-PP tube. FIG. 2D presents the ATR spectrum of the chlorinated MAA-grafted-OH-PP, which is very similar to that of spectrum c (un-chlorinated MAA-grafted-OH-PP).

Figure 4:
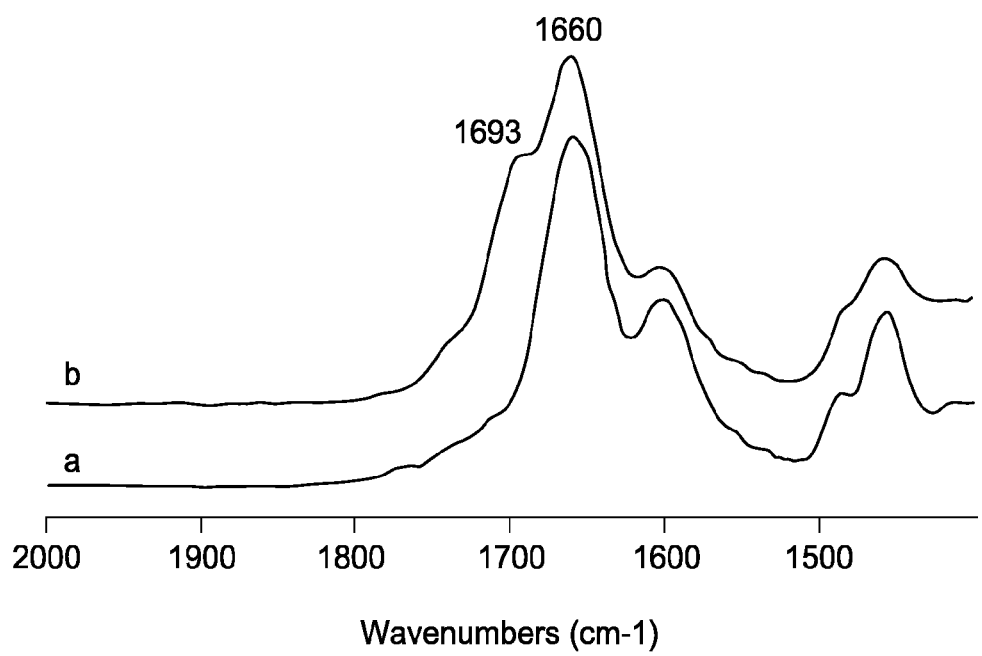
FIGS. 4A and 4B are images of ATR spectra of the surfaces of MAA-grafted-OH-PP tube and chlorinated MAA-grafted-OH-PP tube in the region of 1400 $cm^{-1}$-2000 $cm^{-1}$.

FIG. 4A is an ATR spectrum in the region of 1400 $cm^{-1}$-2000 $cm^{-1}$ of the surfaces of a MAA-grafted-OH-PP tube and FIG. 4B is an ATR spectrum of the surfaces of a chlorinated MAA-grafted-OH-PP tube. In addition to the strong 1660 $cm^{-1}$ peak, spectrum d shows a weak shoulder at 1693 $cm^{-1}$, which can be observed more clearly in the regional ATR spectra of the samples (e.g., particularly the difference between FIG. 4A and FIG. 4B). The 1693 $cm^{-1}$ peak is assigned to the C=O stretching vibration of the chlorinated amide groups (—CONHCl),[45] indicating that upon chorine bleach treatment, some of the amide groups of the grafted MAA side chains were transformed into acyclic N-halamines.

The tubing surfaces were also examined with X-ray Photoelectron Spectroscopy (hereafter referred to as XPS). XPS includes irradiating samples using X-rays and measuring the electron flux. The energy spectrum for the ejected electrons is a combination of an overall trend due to transmission characteristics of the spectrometer, the energy loss of the processes within the sample and the resonance structures of the material under analysis. XPS spectra were obtained on a PHI 5700 x-ray photoelectron spectroscopy system equipped with dual Mg X-ray source and monochromated Al X-ray source.

Figure 5:
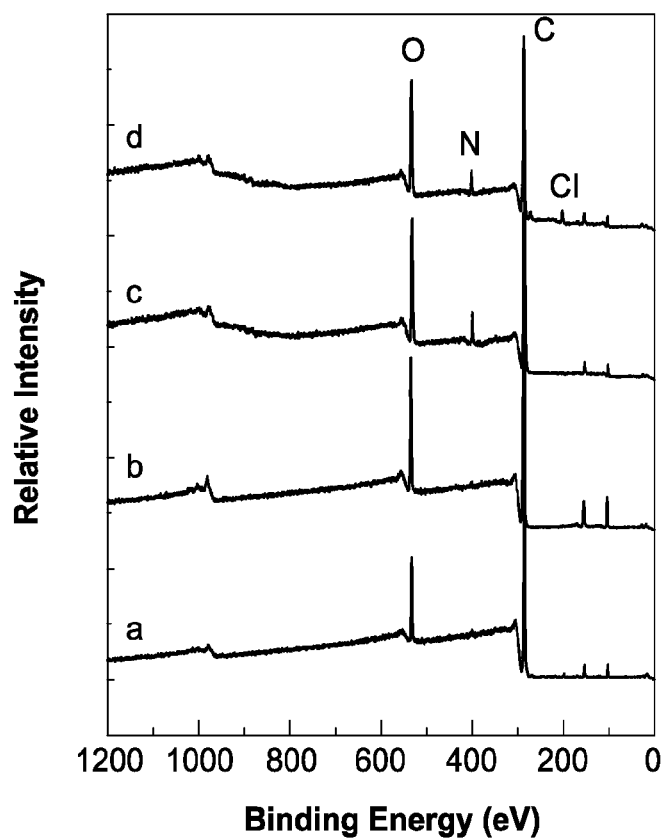
FIGS. 5A-5D are images of XPS spectra of original PP tube, OH-PP tube, MAA-grafted-OH-PP tube and chlorinated MAA-grafted-OH-PP tube.

FIGS. 5A-5D are XPS spectrums of the treated and untreated surfaces. FIG. 5A is a XPS spectrum of original PP, the 285 eV peak is related to carbon atoms, and the band at 533 eV could be caused by oxygen in the air and/or the presence of a small amount of oxidized surface PP molecules generated during the manufacturing process of the samples. FIG. 5B is a XPS spectrum of OH-PP. As expected, after treatment with $K_2S_2O_8$, in the spectrum of OH-PP, the intensity of the oxygen peak is significantly increased. Upon ceric ion-induced MAA grafting treatment, MAA side chains were grafted onto the surfaces of OH-PP. Consequently, a nitrogen peak at 403 $eV^{36}$ appears in the XPS spectrum of MAA-grafted-OH-PP tubing surfaces, as shown in FIG. 5C. In the spectrum of the chlorinated MAA-grafted-OH-PP seen in FIG. 5D, in addition to carbon, oxygen, and nitrogen peaks, a new band at 200 eV can be clearly detected, which is associated with the chlorine atoms in the newly formed acyclic N-halamines. These spectrums illustrate that the N-halamine structures are successfully introduced onto tubing surfaces.

FIGS. 6A-6D are SEM images of the surface of the treated and untreated samples. The inner surfaces and cross-sections of the tubing samples were observed under a LEO 1530 scanning electron microscope (SEM). The samples were fractured in liquid nitrogen and then sputter coated with silver for SEM study.

FIG. 6 presents the morphologies of the inner surfaces and cross-sections of the original PP and the chlorinated-MAA-grafted-OH-PP tubing. FIG. 6A is a SEM image of the inner surface of the original PP tube, while FIG. 6B is an image of the cross-section of the original PP tube. FIG. 6C is an image of the inner surface of the chlorinated MAA-grafted-OH-PP tube, while FIG. 6D is an image of the cross-section of the chlorinated MAA-grafted-OH-PP tube.

Figure 6A:
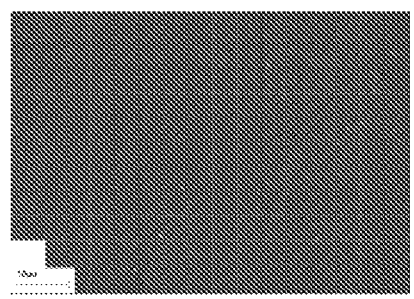
FIGS. 6A-6D are SEM images of inner surface of the original PP tube, cross-section of the original PP tube, inner surface of the chlorinated MAA-grafted-OH-PP tube, and cross-section of the chlorinated MAA-grafted-OH-PP tube.
Figure 6C:
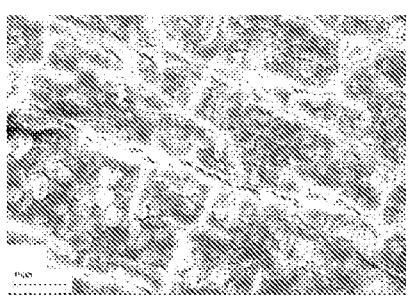
Figure 6B:
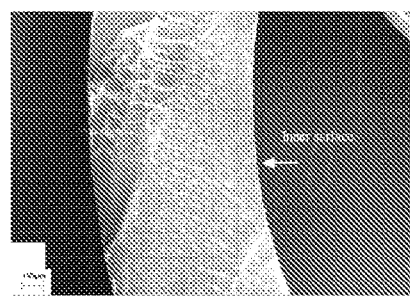
Figure 6D:
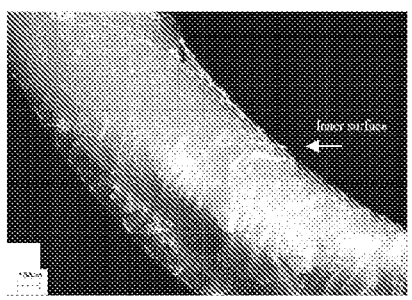

The original PP tubes show a very smooth surface as seen in FIG. 6A. The surface of the chlorinated MAA-grafted-OH-PP tubes as seen in FIG. 6C; however, is much rougher, which could be caused by the hydroxylation/grafting/chlorination reactions and/or the presence of aggregated clusters of grafted MAA side chains. On the other hand, by comparing the cross-sections of the original PP tube FIG. 6B and the chlorinated MAA-grafted-OH-PP tube FIG. 6D, it is concluded that only a very thin (e.g., several micrometers) surface layer of the chlorinated MAA-grafted-OH-PP tubes is affected, suggesting that the hydroxylation, grafting, and chlorination reactions mainly occurred on the surface layer of the tubing.[30]

Bacterial adhesion has been identified as the critical initial step in the formation of biofilms. During this process, cells establish stable interactions with a solid surface by excreting extracellular polymeric substances that anchor themselves to the substratum, which will lead to biofilm formation.[1-3] Consequently, a number of approaches have been attempted in the modification of polymer surfaces in order to prevent/reduce bacterial adhesion, and thus, prevent the formation of biofilms.[3,46-48]

The present invention provides surfaces of chlorinated MAA-grafted-OH-PP tubes contain MAA-based acyclic N-halamines, as seen in FIG. 1. Our previous investigations have demonstrated that after grafting onto textile fabrics, these acyclic N-halamines provided potent biocidal effects.[28] The chlorinated MAA-grafted-OH-PP tubes effectively prevent bacterial adhesion by inactivating microorganisms upon contact. For example, Table 1 summarizes the level of recoverable adherent bacteria from the tubing samples after contacting with $10^6$-$10^7$ CFU/mL of $P.$ $aeruginosa$ for 1 hour.

TABLE I

| Tubing sample | Recoverable adherent bacteria (CFU/cm$^2$) |
|---|---|
| Original PP tube | $(6.6 \pm 0.99) \times 10^4$ |
| Un-chlorinated MAA-grafted-OH-PP tube | $(5.3 \pm 0.81) \times 10^4$ |
| Chlorinated MAA-grafted-OH-PP tube** | $4.0 \pm 0.6$ |

From Table 1 the Recoverable bacteria from the original PP tube, MAA-grafted-OH-PP tube, and chlorinated MAA-grafted-OH-PP tube in the initial adhesion test, where
*$P.$ $aeruginosa$ solution concentration was $10^6$-$10^7$ CFU/mL and the adhesion time was 1 hour and
**the active chlorine content of the chlorinated MAA-grafted-OH-PP tube was 32 μg/cm$^2$.

From the original PP tubes and the un-chlorinated MAA-grafted-OH-PP tubes, as high as $10^4$ CFU/cm$^2$ of adherent $P.$ $aeruginosa$ could be recovered by sonication, suggesting that the test microorganisms have strong abilities to adhere onto these surfaces, which could lead to biofilm formation. However, after chlorination, acyclic N-halamines were formed on the surfaces of the chlorinated MAA-grafted-OH-PP tubes.

Upon contact with $P.$ $aeruginosa$, the positive chlorines of the chlorinated MAA side chains could be transferred to appropriate receptors in the cells, and this reaction could effectively destroy or inhibit the enzymatic or metabolic process, leading to the expiration of the cells.[18] As a result, from the surfaces of the chlorinated MAA-grafted-OH-PP tubes, only about $4.0 \pm 0.6$ CFU/cm$^2$ of adherent $P.$ $aeruginosa$ could be recovered by sonication, indicating that the acyclic N-halamine-based tubing surfaces have potent antimicrobial/anti-adherent effects against the test microorganism.

Figure 7A:
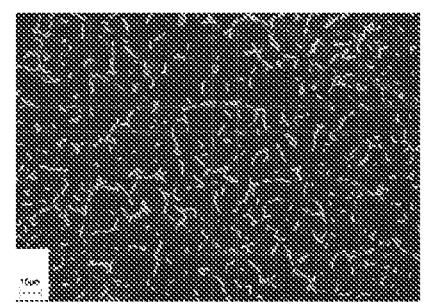
FIGS. 7A to 7D are SEM images of bacterial initial adhesion on original PP tube, original PP tube (observed at higher magnification), MAA-grafted-OH-PP tube, and chlorinated MAA-grafted-OH-PP tube.
Figure 7C:
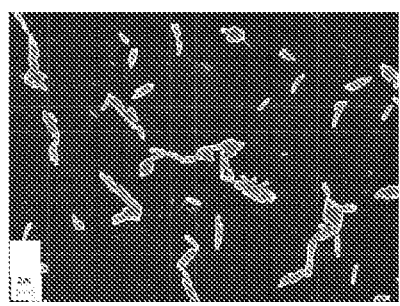
Figure 7B:
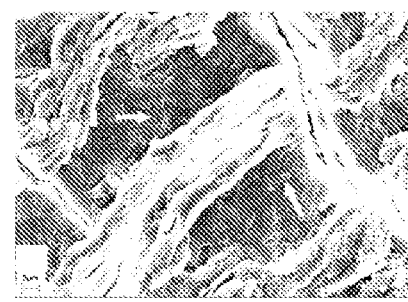
Figure 7D:
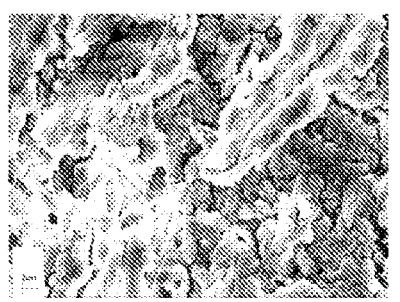

FIGS. 7A-7D are SEM images of the results of bacterial initial adhesion on a surface. FIG. 7A is a SEM images of the results of bacterial initial adhesion on original PP tube, FIG. 7B is a SEM images of the results of bacterial initial adhesion on original PP tube (observed at higher magnification), FIG. 7C is a SEM images of the results of bacterial initial adhesion on MAA-grafted-OH-PP tube, and FIG. 7D is a SEM images of the results of bacterial initial adhesion on chlorinated MAA-grafted-OH-PP tube.

The recoverable adherent bacteria results agree well with SEM observations, as shown in FIG. 7. On the surfaces of the original PP (see FIG. 7A and FIG. 7B) and un-chlorinated MAA-grafted-OH-PP tubes (see FIG. 7C), a large number of adherent bacteria could be observed after 1 hour of contact with $10^6$-$10^7$ CFU/mL of $P.$ $aeruginosa$. On the surfaces of the chlorinated MAA-grafted-OH-PP tube (see FIG. 7D), however, almost no adherent bacteria could be detected.

The antimicrobial/anti-adherent effects of the chlorinated MAA-grafted-OH-PP tubes pointed to biofilm-controlling functions of the samples. To evaluate this, an in vitro bacterial solution flowing model was used to challenge the inner surfaces of the N-halamine-based tubing; the original PP tubing and un-chlorinated MAA-grafted-OH-PP tubes were tested under the same conditions as controls.

Figure 8A:
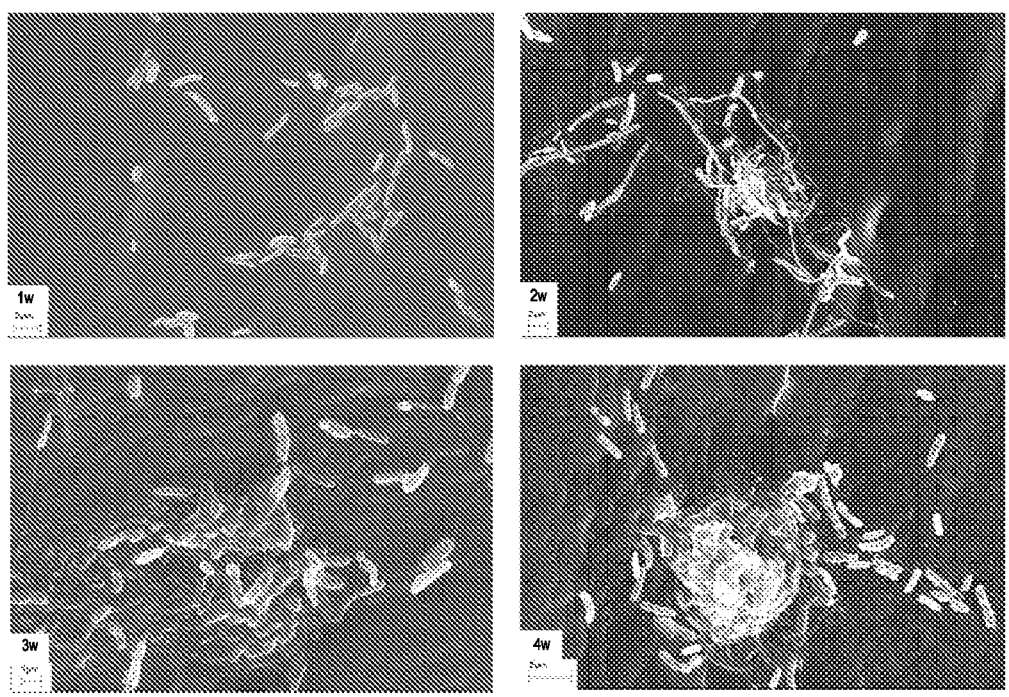
FIGS. 8A-8C are SEM images of the biofilm-controlling functions of the original PP tubing, an un-chlorinated MAA-grafted-OH-PP tubing, and a chlorinated MAA-grafted-OH-PP tubing.
Figure 8B:
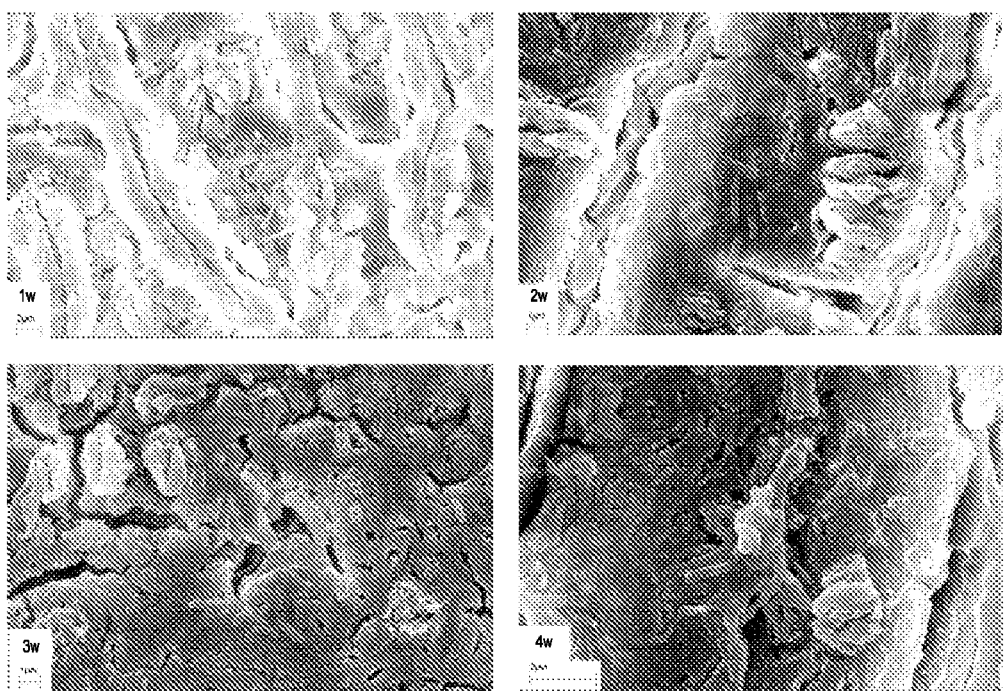
Figure 8C:
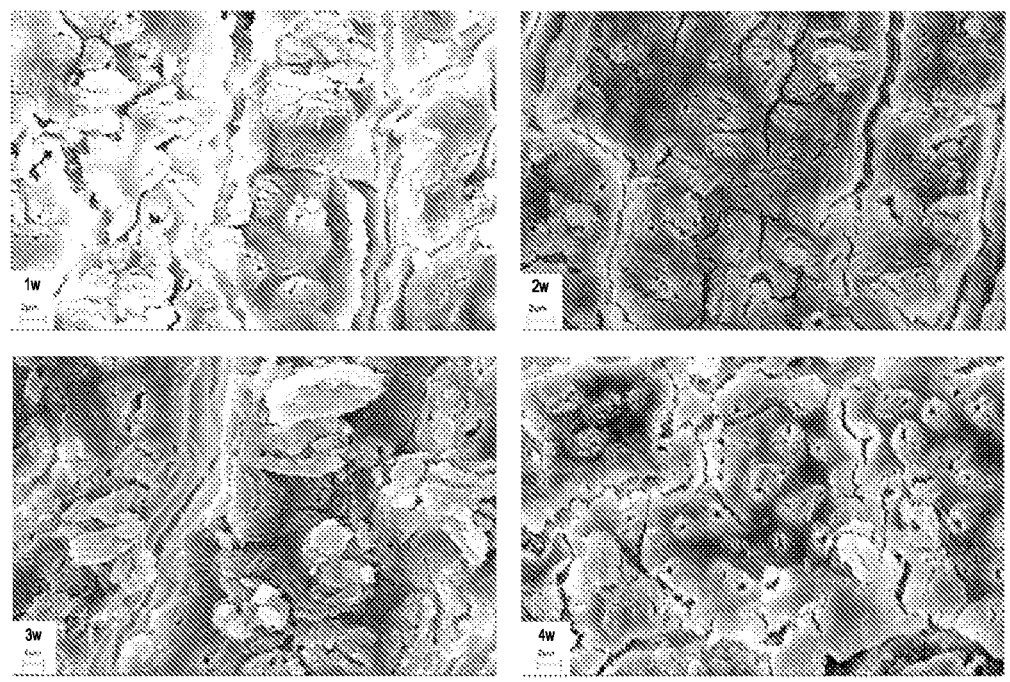

FIGS. 8A-8C are SEM images of the tube surfaces for biofilm-controlling functions after 1, 2, 3, and 4 weeks of bacteria flow. FIG. 8A is an SEM image of the original PP tubing, FIG. 8B, which is an SEM image of an un-chlorinated MAA-grafted-OH-PP tubing, and FIG. 8C is an SEM image of a chlorinated MAA-grafted-OH-PP tubing. For each tubing sample, the bacteria solution was flowed for (1 w) 1 week, (2 w) 2 weeks, (3 w) 3 weeks, and (4 w) 4 weeks.

After 1 week of flow as seen in FIG. 8A, 1 w, $P.$ $aeruginosa$ adhere to the original PP tubing surfaces. At Week 2 as seen in FIG. 8A, 2 w, fiber-like slimes could be observed among the adherent bacteria, which could facilitate surface attachment and micro-colony formation, and protect the organisms within the micro-colonies. With the increase of flowing period, the micro-colonies continue to grow, and biofilms formed after 3 to 4 weeks, as shown in FIG. 8A, 3 w and 4 w.

Similar trends are observed in the un-chlorinated MAA-grafted-OH-PP tubing: As seen in FIG. 8B 1 w-4 w adherent bacteria are detected in week 1 to week 2, FIG. 8B 1 w and 2 w respectively, which develop into biofilms after 3-4 weeks of bacteria flow as seen in FIG. 8B 3 w and 4 w.

Figure 3:
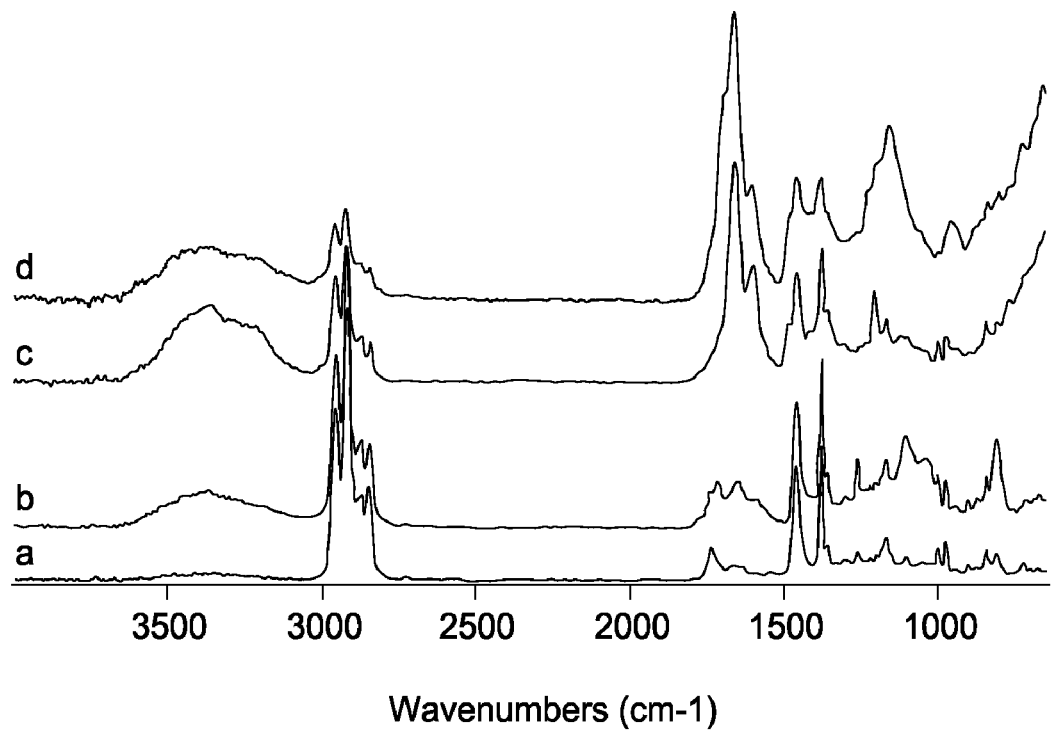
FIGS. 3A to 3D are images of ATR spectra of the surfaces of original PP tube, OH-PP tube, MAA-grafted-OH-PP tube, and chlorinated MAA-grafted-OH-PP tube.

On the chlorinated MAA-grafted-OH-PP tubing surfaces as seen in FIG. 8C, 1 w-4 w, however, no adherent bacteria could be observed in week 1 and week 2 see FIG. 8C, 1 w and 2 w; after 3 to 4 weeks of flow, only scattered adherent bacteria could be observed; no biofilms are presented see FIG. 8C, 3 w-4 w. This suggests that the antimicrobial effects of the N-halamines[18] could effectively prevent the formation of biofilms.

Table 2 presents the level of recoverable adherent $P.$ $aeruginosa$ from the original PP tube, the un-chlorinated MAA-grafted-OH-PP tube, and the chlorinated MAA-grafted-OH-PP tube after different periods of bacteria flow.

TABLE II

Recoverable adherent *P. aeruginosa* after different periods of bacteria flowing (CFU/cm$^2$)

| Tubing | 1 week | 2 weeks | 3 weeks | 4 weeks |
|---|---|---|---|---|
| Original PP tube | $(1.1 \pm 0.17) \times 10^4$ | $(3.3 \pm 0.50) \times 10^4$ | $(7.1 \pm 1.1) \times 10^4$ | $(2.0 \pm 0.3) \times 10^5$ |
| Un-chlorinated MAA-grafted-OH-PP tube | $(4.7 \pm 0.71) \times 10^3$ | $(1.3 \pm 0.20) \times 10^4$ | $(9.3 \pm 1.40) \times 10^4$ | $(1.1 \pm 0.17) \times 10^5$ |
| Chlorinated MAA-grafted-OH-PP tube** | 0 | $5.3 \pm 0.82$ | $(1.3 \pm 0.20) \times 10^2$ | $(5.3 \pm 0.79) \times 10^3$ | where the *P. aeruginosa* concentration in the flow solution was $10^3$-$10^4$ CFU/mL and the active chlorine content of the chlorinated MAA-grafted-OH-PP tube was 32 µg/cm$^2$.

The original PP tubing surfaces provide the highest level of recoverable bacteria. For example, after 1 week of flow, $10^4$ CFU/cm$^2$ of adherent *P. aeruginosa* could be recovered after sonication. With longer flowing time, the level of recoverable bacteria gradually increases, and at week 4, as high as $10^5$ CFU/cm$^2$ of the test organisms could be recovered from the tubing surface.

After grafting with MAA, the surfaces become more hydrophilic, making it more difficult for microbial adhesion. Consequently, in Week 1, less *P. aeruginosa* (e.g., in the range of $10^3$ CFU/cm$^2$; as seen in Table 2) adhered to the surfaces of the un-chlorinated MAA-grafted tubing surfaces; however, in week 2 to week 4, the levels of recoverable bacteria are very similar to those of the original PP tubing surfaces. This suggests that hydrophilic surfaces might be able to reduce initial bacteria adhesion, but once bacteria are attached to the surfaces, these surfaces have little or no effect in preventing the development of micro-colonies and biofilms.

The chlorinated MAA-grafted-OH-PP tubing surfaces showed no bacteria could be recovered from the surfaces in week 1, because of the presence of acyclic N-halamines. In Week 2, the recoverable cells are in the range of about $10^0$ CFU/cm$^2$, and in Week 3, the recoverable level is about $10^2$ CFU/cm$^2$. Even after 4 weeks of bacteria flowing, only $10^3$ CFU/cm$^2$ of adherent bacteria could be recovered from the chlorinated MAA-grafted-OH-PP tubing surfaces after sonication.

The present invention includes a chlorinated MAA-grafted-OH-PP tubing surfaces that effectively prevents or reduces the level of bacterial adhesion and the subsequent biofilm formation for 1-2 weeks when compared to untreated tubing surfaces. Scattered adherent bacteria could be observed on the tubing surfaces, but the level of the adherent bacteria is much lower than that of the original PP tubes and the un-chlorinated MAA-grafted-OH-PP tubes. This trend could be explained by the fact that the biofilm-controlling effects of the new surfaces would consume the covalently bound chlorines; when chlorine contents decrease to lower than a certain limit, bacteria began to adhere to the surfaces, but the level of the adherent bacteria were lower because the residual covalently bound chlorines on the surfaces could still provide antimicrobial functions.

Figure 9:
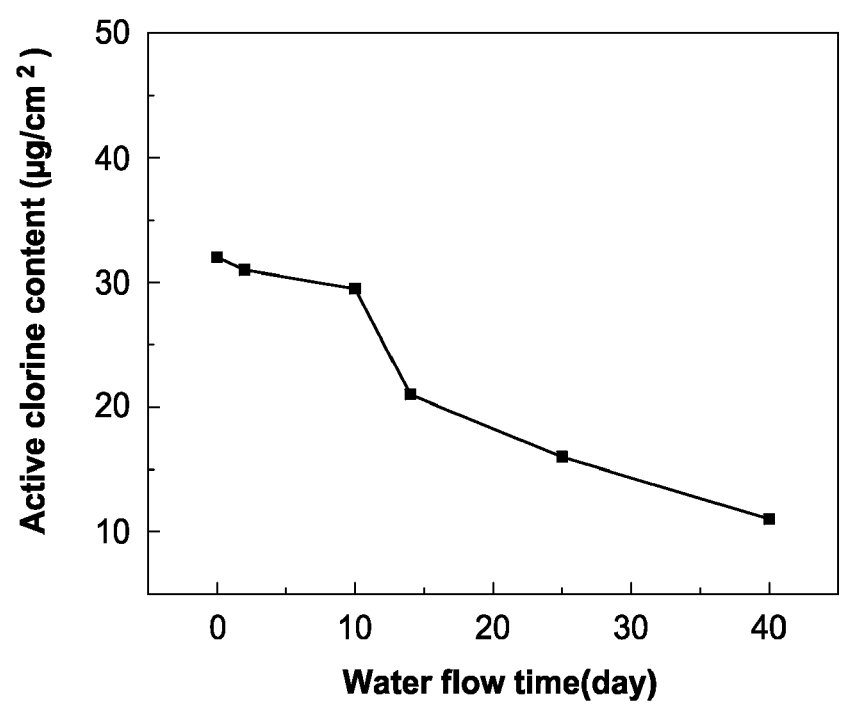
FIG. 9 is a graph of the effects of flowing time on the active chlorine content of the chlorinated MAA-grafted-OH-PP tubes.

The chorine content of the chlorinated MAA-grafted-OH-PP tubing surfaces was determined periodically by iodimetric titration in the flowing test, and the results are shown in the graph of FIG. 9. FIG. 9 is a graph of the effect of flowing time on the active chlorine content of the chlorinated MAA-grafted-OH-PP tubes. The freshly chlorinated surfaces contained 32 µg/cm$^2$ of active chlorine. Increasing flowing time decreases the chlorine content: after 2 weeks of flow, the surfaces had 21 µg/cm$^2$ of active chlorine; and when the flowing time is extended to 40 days, the chlorine content further decreases to 11 µg/cm$^2$, suggesting that chlorine content is the decisive factor of the biofilm-controlling functions of the acyclic N-halamine-based tubing materials. The flowing water was also tested weekly with a pocket photometer (Fisher Scientific), which showed that the total chlorine residue content in the flowing water was less than 1.0 ppm during the study period of 40 days.

Although longer flowing time could decrease biofilm-controlling functions due to the consumption of covalently bound chlorines on the N-halamine-based tubing surfaces, all the consumed chlorines could be recharged by using bleaching conditions as those in the preparation of the chlorinated MAA-grafted-OH-PP tubing. After 10 days of bacteria flowing, the chlorinated MAA-grafted-OH-PP tubing (the sample) and the original PP tubing (the control) were re-chlorinated, and the biofilm-controlling functions of the re-chlorinated control and sample tubes were reevaluated.

Figure 10A:
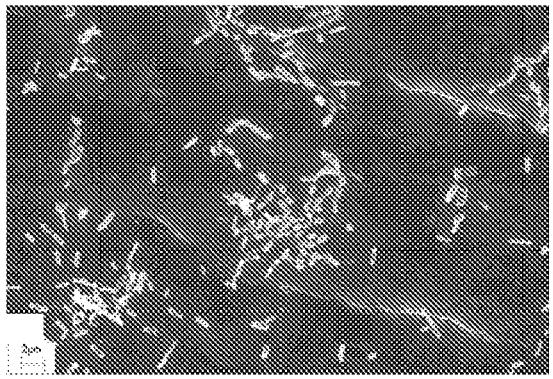
FIGS. 10A-10F are SEM images of the biofilm-controlling functions of the re-chlorinated original PP tubing and the re-chlorinated MAA-grafted-OH-PP tubing after different recharging treatments.
Figure 10D:
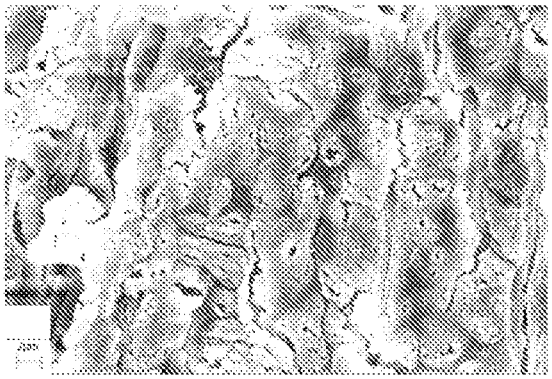
Figure 10B:
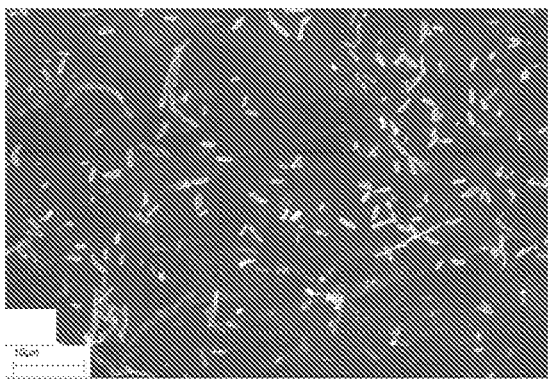
Figure 10E:
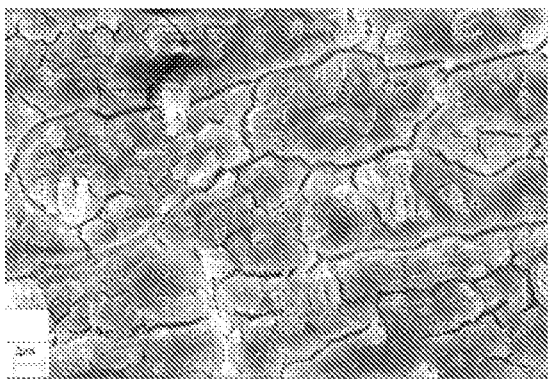
Figure 10C:
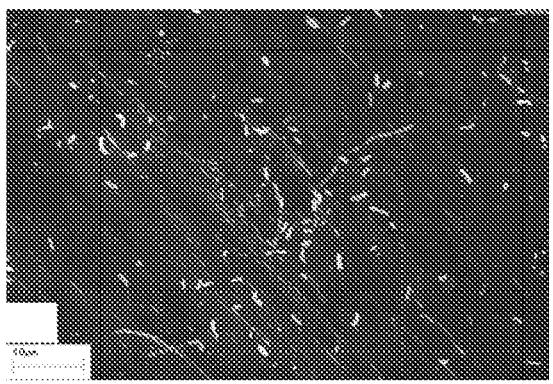
Figure 10F:
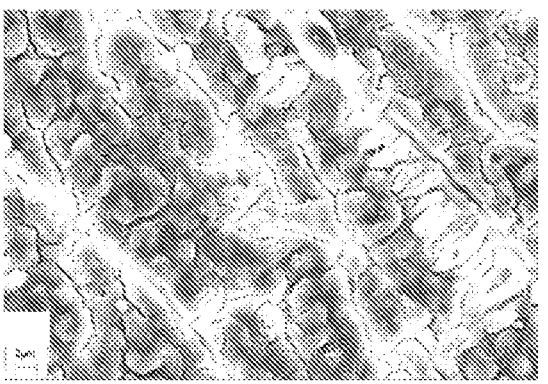

FIGS. 10A-10F are SEM images of the influences of re-chlorination on the biofilm-controlling functions of the control (re-chlorinated original PP) tubing and the sample (re-chlorinated MAA-grafted-OH-PP) tubing. FIGS. 10A, 10B and 10C are SEM images of the biofilm-controlling functions of the re-chlorinated original PP tubing. FIGS. 10D, 10E and 10F are SEM images of the re-chlorinated MAA-grafted-OH-PP tubing. After one recharging treatment as seen in the SEM images of FIG. 10A and FIG. 10D, after two recharging treatments as seen in the SEM images of FIG. 10B and FIG. 10E, and after three recharging treatments as seen in the SEM images of FIG. 10C and FIG. 10F. After each recharging, $10^3$-$10^4$ CFU/mL of *P. aeruginosa* flowed through the tubing samples for 10 days.

FIGS. 10A-10F is shows the SEM results of the influences of re-chlorination on the biofilm-controlling functions of the control (re-chlorinated original PP) tubing and the sample (re-chlorinated MAA-grafted-OH-PP) tubing. On the re-chlorinated control tubing (FIGS. 10A, 10B and 10C: re-chlorinated 1, 2, and 3 times, respectively), after 10 days of flowing, a large quantity of adherent bacteria could be observed on the tubing surfaces. On the re-chlorinated sample tubing (FIGS. 10D, 10E and 10F), however, no adherent bacteria could be detected, suggesting that the biofilm-controlling functions of the chlorinated MAA-grafted-OH-PP tubing are fully rechargeable.

Table 3 illustrates the level of recoverable adherent *P. aeruginosa* bacteria from the original PP tubes and chlorinated MAA-grafted-OH-PP tubes after different re-chlorination treatments.

TABLE III

| Tubing | Level of recoverable *P. aeruginosa* (CFU/cm$^2$) | | |
|---|---|---|---|
| | Re-chlorinated once | Re-chlorinated twice | Re-chlorinated three times |
| Original PP tube | $(2.0 \pm 0.3) \times 10^4$ | $(5.2 \pm 0.78) \times 10^4$ | $(8.0 \pm 1.2) \times 10^4$ |
| Chlorinated MAA-grafted-OH-PP tube | 0 | 0 | $4.6 \pm 0.69$ | where the *P. aeruginosa* concentration in the flowing solution was $10^3$-$10^4$ CFU/mL; the bacteria flow time after each re-chlorination was 10 days.

After one re-chlorination treatment, the control tubing shows $(2.0\pm0.3)\times10^4$ CFU/cm$^2$ of recoverable adherent bacteria after 10 days of bacteria flow; after two recharging treatments, the level of recoverable adherent bacteria is $(5.2\pm0.78)\times10^4$ CFU/cm$^2$; and after three recharging treatments, as high as $(8.0\pm1.2)\times10^4$ CFU/cm$^2$ of adherent bacteria could be recovered from the same tubing surfaces. This increasing trend in the level of recoverable adherent bacteria after each re-chlorination treatment implies that during the re-chlorination treatment, although diluted bleach could inactivate most of the adherent bacteria, some of the exopolysaccharide glycocalyx polymers and other residues secreted by the adherent bacteria could still attach to the tubing surfaces, making it easier for *P. aeruginosa* to adhere onto the surfaces of the control tubing in the subsequent bacteria flowing tests.

On the recharged chlorinated MAA-grafted-OH-PP tubing, however, almost no adherent bacteria could be recovered after 10 days of bacteria flow. Repeated recharging does not seem to significantly affect the results. These findings further confirm that the chlorinated MAA-grafted-OH-PP tubes have potent and rechargeable biofilm-controlling functions against *P. aeruginosa*.

The present invention includes composition contained within the acrylamide/amine class. More particularly, a method and composition are provided that include a class of methacrylamide (MAA)-based biocidal materials. MAA is polymerized to form its homopolymer, polymethacrylamide (PMAA), MAA is copolymerized with other polymerizable monomers to form copolymers or MAA is grafted onto other polymeric materials with or without the presence of other monomers to form graft copolymers. The resultant MAA-based polymers can be used alone, blended/mixed with other materials, or co-bonded with other compositions. Upon exposure to halogen source(s), acyclic N-halamines are formed in the MAA-based materials, which can provide durable and rechargeable biocidal effects against bacteria, spores, fungi, yeasts, and virus.

To transform part of the bonded MAA moieties in the surface into acyclic N-halamines, the surfaces were contacted with a NaOCl solutions (between about 0.1 and 10%, e.g., about 0.6%). In some instances, about 0.05% of a nonionic wetting agent (Triton X-100) was added. The pH values of the solutions were adjusted with pH buffers. After chlorination, the surfaces were washed thoroughly with distilled water.

The effects of varying CAN concentration can affect the binding reactions. Percentage graft yield increases and then decreases after an optimum value of 2.0×10-3 mol/L. For example, when the concentration of CAN is higher than the optimum value, further increase in initiator concentration may generate too much free radical, which will terminate the growing MAA side chains. Besides, high free radical concentration can promote chain transfer reactions to the monomers, which will result in the homopolymerization of MAA in the solutions and thereby decrease the concentrations of available MAA for the binding reactions.

The object and/or the surface may be in part or entirely include Polyethylene (PE); Polypropylene (PP); Polystyrene (PS); Polyethylene terephthalate (PET or PETE); Polyamide (PA); Polyester Polyvinyl chloride (PVC); Polycarbonate (PC); Acrylonitrile butadiene styrene (ABS); Polyvinylidene chloride (PVDC); Polytetrafluoroethylene (PTFE); Polymethyl methacrylate (PMMA); Polylactic acid (PLA) and combinations thereof. In addition, the Polyethylene (PE); Polypropylene (PP); Polystyrene (PS); Polyethylene terephthalate (PET or PETE); Polyamide (PA); Polyester Polyvinyl chloride (PVC); Polycarbonate (PC); Acrylonitrile butadiene styrene (ABS); Polyvinylidene chloride (PVDC); Polytetrafluoroethylene (PTFE); Polymethyl methacrylate (PMMA); Polylactic acid (PLA) may be modified, substituted or altered by the skilled artisan.

Nitrogen-containing compounds include poly(oxyethylene) (meth)acrylates, N-methylol acrylamide, N-methylol methacrylamide, N-butoxymethyl acrylamide, hydroxylethyl (meth)acrylate, 2-hydroxybutyl(meth)acrylate, 2-hydroxypropyl(meth)acrylate, 3-chloro-2-hydroxypropyl (meth)acrylate, and glycidyl(meth)acrylatemethacrylamide, t-butylaminoethyl methacrylate, dimethylaminoethyl methacrylate, diethylaminoethyl methacrylate, N,N-dimethylaminopropyl methacrylamide, 2-t-butylaminoethyl methacrylate, N,N-dimethylaminoethyl acrylate, 2-acrylamido-2-methylpropanesulfonic acid, and the like.

For example the monomers may include one or more selected from: methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, glycidyl acrylate, 2-hydroxyethyl acrylate, hydroxypropyl acrylate (all isomers), hydroxybutyl acrylate (all isomers), diethylaminoethyl acrylate, triethyleneglycol acrylate, N-tert-butyl acrylamide, N-n-butyl acrylamide, N-methyl-ol acrylamide, N-ethyl-ol acrylamide, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, styrene, diethylamino styrene, para-methylstyrene, vinyl benzoic acid, vinyl benzene sulfonic acid, vinyl propionate, vinyl butyrate, vinyl benzoate, vinyl chloride, vinyl fluoride, vinyl bromide, methyl methacrylate, ethyl methacrylate, propyl methacrylate, butyl methacrylate, 2-ethylhexyl methacrylate, isobornyl methacrylate, methacrylic acid, benzyl methacrylate, phenyl methacrylate, methacrylonitrile, alpha methyl styrene, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, isopropenyl butyrate, isopropenyl acetate, isopropenyl benzoate, isopropenyl chloride, isopropenyl fluoride, isopropenyl bromideitaconic aciditaconic anhydridedimethyl itaconate, methyl itaconate N-tert-butyl methacrylamide, N-n-butyl methacrylamide, N-methyl-ol methacrylamide, N-ethyl-ol methacrylamide, isopropenylbenzoic acid, diethylamino alphamethylstyrene, para-methyl-alpha-methylstyrene, diisopropenylbenzene, isopropenylbenzene sulfonic acid, methyl 2-hydroxymethylacrylate, ethyl 2-hydroxymethylacrylate, propyl 2-hydroxymethylacrylate, butyl 2-hydroxymethylacrylate, 2-ethylhexyl 2-hydroxymethylacrylate, isobornyl 2-hydroxymethylacrylate, and dimethyl Meta-Isopropenyl-benzyl Isocyanate.

The present invention also provides a method of controlling microbial contamination of a surface by functionalizing a surface of an object and binding one or more acyclic-amine structures to the surface. The one or more acyclic-amine structures are halogenated to form one or more acyclic N-halamine structures. The one or more acyclic N-halamine structures modulates the formation of a biofilm.

The present invention provides a method of controlling microbial contamination of a surface or a portion of a surface. For example, the surface may be a portion of an object (e.g., a wall, a bottom, a heater, a chiller, a plate, a bath, a pipe, a conduit etc.) or the entire object, a bath, a pump, a tube, a condenser, a collector, etc. For example, a conduit includes tubes, waterways, canals, pipes, aqueducts, covers, ducts. The surface and or the object may include polyethylene; polypropylene; polystyrene; polyethylene terephthalate; polyamide; polyester Polyvinyl chloride; polycarbonate; acrylonitrile butadiene styrene; polyvinylidene chloride; polytetrafluoroethylene; polymethyl methacrylate; polylactic acid and combinations thereof.

The acyclic N-halamine compound includes one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof including acyclic N-halamine compound further modified by the addition of one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Hall-Stoodley L, Costerton J W, Stoodley P. Bacterial biofilms: from the natural environment to infectious diseases. Nature Rev Microbiol 2004; 2:95-108.

2. Van Loosdrecht M C M, Lyklema J, Norde W, Zehnder A J B. Influence of interfaces on microbial activity. Microbiol. Rev 1990; 54:75-87.

3. An Y H, Friedman R J, ed. Handbook of Bacterial Adhesion: Principles, Methods, and Applications. Totowa N.J.: Humana Press Inc; 2000.

4. Ramagea G, Tunneyb M M, Patricka S, Gormanb S P, Nixonc J R. Formation of *Propionibacterium acnes* biofilms on orthopaedic biomaterials and their susceptibility to antimicrobials. Biomaterials 2003; 24:3221-3227.

5. Gorman S P, McGovern J G, Woolfson A D, Adair C G, Jones D S. The concomitant development of poly(vinyl chloride)-related biofilm and antimicrobial resistance in relation to ventilator-associated pneumonia. Biomaterials 2001; 22:2741-2747.

6. Blake G C. The incidence and control of bacteria infection of dental units and ultrasonic scalers. Br Dent J 1963; 115:413-416.

7. Mills S E. The dental unit waterline controversy: defusing the myths, defining the solutions. J Am Dent Assoc 2000; 131:1427-1441.

8. Depaola L G, Mangan D, Mills S E, Costerton W, Barbeau J, Shearer B, Bartlett J. A review of the science regarding dental unit waterlines. J Am Dent Assoc 2002; 133:1199-1206.

9. Williams J F, Johnston A M, Johnson B, Huntington M K, Mackenzie C D, Path M R C. Microbial contamination of dental unit waterlines: prevalence, intensity and microbiological characteristics. J Am Dent Assoc 1993; 124:59-65.

10. Shearer B G. Biofilm and the dental office. J Am Dent Assoc 1996; 127:181-189.

11. ADA council on scientific affairs. Dental unit waterlines: approaching the year 2000. J Am Dent Assoc 1999; 130:1653-1664.

12. Robert H W, Karpay R1, Mills S E. Dental unit waterline antimicrobial agent: effect on dentin bond strength. J Am Dent Assoc 2000; 131:179-183.

13. Karpay R1, Plamondon T J, Mills S E, Dove S B. Combining periodic and continuous sodium hypochlorite treatment to control biofilms in dental unit water systems. J Am Dent Assoc 1999; 130:957-965.

14. Linger J B, Molinari J A, Forbes W C, Farthing C F, Winget W J. Evaluation of a hydrogen peroxide disinfectant for dental unit waterlines. J Am Dent Assoc 2001; 132:1287-1291.

15. Ozcan M, Kulak Y, Kazazoglu E. The effect of disinfectant agents in eliminating the contamination of dental unit water. J Oral Rehabili 2003; 30:290-294.

16. Walker J T, Bradshaw D J, Fulford M R, Marsh P D. Microbiological evaluation of a range of disinfectant products to control mixed-species biofilm contamination in a laboratory model of a dental unit water system. Appl Environ Microbiol 2003; 69:3327-3332.

17. Puttaiah R, Karpay R I, Fabre C, Sherman L R, Nemeth J F, Mills S E, Plamondon T J. Dental unit water line treatment with sodium hypochlorite and acetic acid. Microchem J 1998; 59:333-340.

18. Worley S D, Williams D E. Halamine water disinfectants. CRC Crit. Rev Environ Control 1988; 18:133-175.

19. Burkett H D, Faison J H, Kohl H H, Wheatley W B, Worley S D, Bodor N. A novel chloramine compound for water disinfection. Water Resource Bull 1981; 17:874-879.

20. Worley S D, Burkett H D, Price J F. The tendency of a new water disinfectant to produce toxic trihalomethanes. Water Resource Bull 1984; 20:369-371.

21. Sun Y Y, Chen T, Worley S D, Sun G. Novel refreshable N-halamine polymeric biocides containing imidazolidin-4-one derivatives. J Polym Sci: Part A 2001; 39:3073-3084.

22. Chen Z B, Sun Y Y. N-Chloro-hindered amines as multifunctional polymer additives. Macromolecules 2005; 38:8116-8119.

23. Sun G, Xu X, Bickert J R, Williams J F. Durable and regenerable antibacterial finishing of fabrics with a new hydantoin derivative. Ind Eng Chem Res 2001; 40:1016-1021.

24. Lin J, Winkelman C, Worley S D, Broughton R M, Williams J F. Antimicrobial treatment of nylon. J Appl Polym Sci 2001; 81:943-947.

25. Sun Y Y, Sun G. Durable and regenerable antimicrobial textile materials prepared by a continuous grafting process. J Appl Polym Sci 2002; 84:1592-1599.

26. Braun M, Sun Y Y. Antimicrobial polymers containing melamine derivatives. I. Preparation and characterization of chloromelamine-based cellulose. J Polym Sci Part A: Polym Chem 2004; 42:3818-3827.

27. Sun Y Y, Sun G. Synthesis, characterization, and antibacterial activities of novel N-halamine polymer beads prepared by suspension copolymerization. Macromolecules 2002; 35:8909-8912.

28. Luo J, Sun Y Y. Acyclic N-halamine-based fibrous materials: preparation, characterization, and biocidal functions. J Polym Sci: Part A Polym Chem 2006; 44:3588-3600.

29. Barbeau J, Gauthier C, Payment P. Biofilms, infectious agent, and dental unit waterlines: a review. Can J Microbiol 1998; 44:1019-1028.

30. Bamford C H, Al-Lamee K G. Studies in polymer surface functionalization and grafting for biomedical and other applications. Polymer 1994; 35:2844-2852.

31. Benson D E, Burns G L, Mohammad S F. Effects of plasma on adhesion of biofilm forming *Pseudomonas aeruginosa* and *Staphylococcus* epidermidis to fibrin substrate. ASAIO J 1996; 42: M655-660.

32. Richmond J Y, McKinney R W. Biosafaty in Microbiological and Biomedical Laboratories, 4th ed. Washington D.C.: U.S. Government Printing Office, 1999.

33. Yorganci K, Krepel C, Weigelt J A, Edmiston C E. Activity of antibacterial impregnated central venous catheters against *Klebsiella pneumoniae*. Intensive Care Med 2002; 28:438-442.

34. Tollefson D F, Bandyk D F, Kaebnick H W, Seabrook G R, Towne J B. Surface biofilm disruption: Enhanced recovery of microorganisms from vascular prostheses. Arch Surg 1987; 122:38-43.

35. Cen L, Neoh K G, Kang E T. Antibacterial activity of cloth functionalized with N-alkylated poly(4-vinylpyridine). J Biomed Mater Res 2004; 74A:70-80.

36. Dhamodharan R, Nisha A, Pushkala K, McCarthy T J. Investigation of the mercat reaction as a tool for the introduction of nitrogen surface functionality on linear low-density polyethylene (LLDPE) and polypropylene (PP), Langmuir 2001; 17:3368-3374.

37. Bergbreiter D E, Walchuk B, Holtzman B, Gray N H. Polypropylene surface modification by entrapment functionalization. Macromolecules 1998; 31:3417-3423.

38. Li Y, Desimone J M, Poon C D, Samulski E T. Photoinduced graft polymerization of styrene onto polypropylene substrates. J Appl Polym Sci 1997; 64:883-889.

39. Chun H J, Cho S M, Lee Y M, Lee H Y, Suh T S, Shinn K S. Graft copolymerization of mixtures of acrylic acid and acrylamide onto polypropylene film. J Appl Polym Sci 1999; 72: 251-256.

40. Tao G, Gong A, Lu J, Sue H J, Bergbreiter D E. Surface functionalized polypropylene: Synthesis, characterization, and adhesion properties. Macromolecules 2001; 34:7672-7679.

41. Johnsen K, Kirkhorn S, Olafsen K, Redford K, Stori A. Modification of polyolefin surfaces by plasma-induced grafting. J Appl Polym Sci 1996; 59:1651-1657.

42. Amomsakchai T, Liewcharoen N, Phinyocheep P. Surface modification of low density polyethylene using accelerated decomposition of potassium persulfate and ceric ion induced acrylamide grafting. J Mater Sci Lett 2002; 21:1035-1038.

43. Hintz H L, Johnson D C J. The Mechanism of oxidation of cyclic alcohols by Cerium (IV). Org Chem 1967; 32:556-564.

44. Hass H H, MacDonald R L. Imidization reaction in polyvinylamides. J Polym Sci Part A-1: Polym Chem 1971; 9:3583-3593.

45. Lin J, Cammarata V, Worley S D. Infrared characterization of biocidal nylon. Polymer 2001; 42:7903-7906.

46. Vigo T L. Advances in antimicrobial polymers and materials. In: Gebelein C, Carraher C, ed. Biotechnology and Bioactive Polymers. New York: Plenum Press; 1994. p 225-237.

47. Baumgartner J N, Yang C Z, Cooper S L. Physical property analysis and bacterial adhesion on a series of phosphonated polyurethanes. Biomaterials 1997; 18:831-837.

48. Jansen B, Kohnen W. Prevention of biofilm formation by polymer modification. J Ind Microbiol 1995; 15:391-396.

What is claimed is:

1. A method of controlling microbial contamination of a tubing surface comprising the steps of:
    functionalizing at least a portion of an inner surface of a tube;
    binding one or more methacrylamides to the inner surface; and
    halogenating the one or more methacrylamides to form one or more acyclic N-halamines, wherein the one or more acyclic N-halamines modulate the growth of a biofilm on the inner surface of the tube.

2. The method of claim 1, wherein the acyclic N-halamine compound comprises one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

3. The method of claim 1, wherein the acyclic N-halamine compound is further modified by the addition of one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

4. The method of claim 1, wherein the inner surface comprises polyethylene; polypropylene; polystyrene; polyethylene terephthalate; polyamide; polyester Polyvinyl chloride; polycarbonate; acrylonitrile butadiene styrene; polyvinylidene chloride; polytetrafluoroethylene; polymethyl methacrylate; polylactic acid and combinations thereof.

5. A method of controlling microbial contamination of a surface comprising the steps of:
    functionalizing a surface of an object;
    binding one or more acyclic-amine structures to the surface; and
    halogenating the one or more acyclic-amine structures to form one or more acyclic N-halamine structures, wherein the one or more acyclic N-halamine structures modulates the formation of a biofilm.

6. The method of claim 5, further comprising the step of recharging the one or more acyclic-amine structures with one or more halogens to form the one or more acyclic N-halamine structures.

7. The method of claim 5, wherein the object is a tube, a wall, a bottom, a heater, a chiller, a plate, a bath, a pipe, a conduit or a combination thereof.

8. The method of claim 5, wherein the one or more acyclic-amine structures comprise methacrylamide.

9. The method of claim 5, wherein the one or more acyclic N-halamines comprise and specific compounds.

10. The method of claim 5, wherein the acyclic N-halamine compound comprises one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

11. The method of claim 5, wherein the acyclic N-halamine compound is further modified by the addition of one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

12. The method of claim 5, wherein the surface comprises polyethylene; polypropylene; polystyrene; polyethylene terephthalate; polyamide; polyester Polyvinyl chloride; polycarbonate; acrylonitrile butadiene styrene; polyvinylidene chloride; polytetrafluoroethylene; polymethyl methacrylate; polylactic acid and combinations thereof.

13. The method of claim 5, wherein the step of halogenating comprises the addition of a halide solution comprising fluorine, chlorine, bromine, iodine, astatine, or a combination thereof.

14. The method of claim 5, wherein the step of halogenating comprises the addition of a halide source comprises sodium di-X-isocyanurate, sodium hypohalite, N—X-succinimide, or calcium hypohalite, wherein X is selected from Cl, I or Br.

* * * * *